(12) United States Patent
Tsuchida et al.

(10) Patent No.: US 6,933,352 B2
(45) Date of Patent: Aug. 23, 2005

(54) AMPHIPHILIC COMPOUNDS HAVING A DENDRITIC BRANCH STRUCTURE

(75) Inventors: Eishun Tsuchida, Tokyo (JP); Shinji Takeoka, Tokyo (JP); Keitaro Sou, Tokyo (JP); Haruki Ohkawa, Tokyo (JP)

(73) Assignee: Japan Science and Technology Corporation, Kawaguchi (JP)

( * ) Notice: Subject to any disclaimer, the term of this patent is extended or adjusted under 35 U.S.C. 154(b) by 119 days.

(21) Appl. No.: 10/083,555

(22) Filed: Feb. 27, 2002

(65) Prior Publication Data

US 2002/0120096 A1 Aug. 29, 2002

Related U.S. Application Data

(63) Continuation of application No. PCT/JP00/05702, filed on Aug. 24, 2000.

(30) Foreign Application Priority Data

Aug. 31, 1999 (JP) .............................. 11-245731

(51) Int. Cl.$^7$ .......................... C08L 77/00; C08G 69/44
(52) U.S. Cl. ...................... 525/420; 528/288; 528/291; 528/292; 525/437; 525/540
(58) Field of Search ............... 528/288, 291, 528/292; 525/420, 437, 540

(56) References Cited

U.S. PATENT DOCUMENTS 5,229,490 A 7/1993 Tam

FOREIGN PATENT DOCUMENTS

| JP | 7-505915 | 6/1995 |
| JP | 11-296638 | 2/1999 |
| JP | 11-71519 | 3/1999 |
| WO | WO 93/21144 | 10/1993 |
| WO | WO 93/21259 | 10/1993 |
| WO | WO 94/17125 | 8/1994 |

OTHER PUBLICATIONS

Silvius et al, "Interbilayer Transfer of Phospholipid–Anchored Macromolecules Via Monomer Diffusion", Biochemistry 1993, 32, 3153–3161.
Issberner et al, "Dendrimers" From Generations and Functional Groups to Functions, Angew. Chem. Int. Ed. Engl. 1994, 33, No. 23/24.
Tam, "Synthetic Peptide Vaccine Design: Synthesis and Properties of a High–Density Multiple Antigenic Peptide System", Proc. Natl. Acad. Sci., USA, vol. 85, pp. 5409–5413, Aug. 1988.
Gitsov et al, "Novel Polyether Copolymers Consisting of Linear and Dendritic Blocks," Angew. Chem. Int. Ed. Engl. 1992, 31, No. 9.
Chapman et al, "Hydraamphiphiles: Novel Linear Dendritic Block Copolymer Surfactants". J. Am. Chem. Soc. 1994, 116, 11195–11196.
Schenning et al, "Amphiphilic Dendrimers as Building Blocks in Supramolecular Assemblies", J. Am. Chem. Soc. 1998, 120, 8199–8208.
Singh, "Terminal Groups in Starburst Dendrimers: Activation and Reactions with Proteins", Bioconjugate Chem. 1998, 9, 54–63.

*Primary Examiner*—Samuel A. Acquah
(74) *Attorney, Agent, or Firm*—Oblon, Spivak, McClelland, Maier & Neustadt, P.C.

(57) ABSTRACT

An amphiphilic compound having a dendritic branch structure represented by general formula (I):

$$R_0 - \left[ \begin{array}{c} R_1 \\ R_2 \end{array} \right]_n \quad (I)$$

In the formula (I), $R_0$ is a hydrophilic group; $R_1$ and $R_2$ are independently a hydrophobic group; and n is an integer of 1 to 4. This amphiphilic compound is capable of stably fixing a water-soluble polymer onto a surface structure by taking advantage of intermolecular interaction, thereby enabling the water-soluble polymer to be carried thereon without giving any damage to the function thereof.

16 Claims, No Drawings

US 6,933,352 B2

AMPHIPHILIC COMPOUNDS HAVING A DENDRITIC BRANCH STRUCTURE

CROSS-REFERENCE TO RELATED APPLICATIONS

This is a Continuation Application of PCT Application No. PCT/JP00/05702, filed Aug. 24, 2000, which was not published under PCT Article 21(2) in English.

This application is based upon and claims the benefit of priority from the prior Japanese Patent Application No. 11-245731, filed Aug. 31, 1999, the entire contents of which are incorporated herein by reference.

BACKGROUND OF THE INVENTION

1. Field of the Invention

The present invention relates to an amphiphilic compound having a dendritic branch structure.

2. Description of the Related Art

The amphiphilic compound having a dendritic branch structure according to the present invention is useful for stably fixing, e.g., a water-soluble polymer or oligomer, a polysaccharide or a water-soluble protein on phospholipid vesicles, cell surfaces or hydrophobic surfaces with a minimum modification of these materials. Further, the amphiphilic compound having a dendritic branch structure according to the present invention is also useful as a surface modifier for various substances including, for example, a vesicle or microsphere exhibiting a specific recognizing ability to cells or proteins, a gel for column separation, various sensors and a cell culture substrates, and is also useful as an emulsifier, a stabilizer, a dispersant, a solubilizer, an admixture, a wetting agent, a penetrating agent, or a viscosity modifier for go medicines, foods, cosmetics and dyes.

Surfaces modified with a water-soluble polymer chain such as polyoxyethylene are excellent in biocompatibility, and can be utilized as a raw material for, e.g., an artificial organ (e.g., artificial vessel), an artificial cell, or an artificial blood. Further, by introducing a functional molecule into the surface, the surface can be furnished with a specific function. The introduction of such a water-soluble polymer chain to the surface is usually performed through a covalent bond. It can be said that a methodology for stably fixing such a water-soluble polymer chain to the surface by utilizing intermolecular interaction has not yet been established until now.

As is well known, a vesicle with phospholipid bilayer membrane is accompanied with various problems that it often aggregates or fuses, and that the residence time thereof in blood is relatively short. These problems have been solved by mixing charged lipid or cholesterol into the lipid component constituting the vesicle, and modifying the surface of the vesicle with polyoxyethylene or saccharide. A lipid composed of diacylphosphatidylethanolamine or cholesterol having polyoxyethylene bonded thereto is widely employed as a stabilizer for vesicles. It is reported however that the diacyl lipid having such a water-soluble polymer bonded thereto is eliminated from the phospholipid vesicle (J. R. Silvius and M. J. Zuckermann, Biochemistry, 32, 3153, 1993).

It is now extensively studied that a functional protein (or a portion thereof) that is capable of recognizing a specific molecule or a specific cell surface is carried on a surface of a vesicle, which is utilized as a drug transporter or as artificial cells. Further, since it is generally difficult to procure such a functional protein from cells, and hence only a trace amount is obtainable from cells, it is now adopted a method (recombinant system) wherein only a water-soluble recognizing function site of the protein is permitted to secrete into gene recombinant fungus to produce a large amount of the functional protein. In order to carry this water-soluble protein on the surface of phospholipid vesicle bilayer membrane, it is required to introduce a hydrophobic group into the membrane. For example, a method of coupling a lipid (diacylphosphatidylethanolamine) to the amino group, carboxyl group or thiol group of protein by an appropriate means has been frequently employed. However, since the phospholipid employed in this case is double-legged, it is required, in order to stably introduce the hydrophobic group into the surface of bilayer membrane, that the lipid be coupled at a plurality of sites so as to well-balance the hydrophobic site with the hydrophilic site. If this coupling is performed non-selectively, the functions are often impaired by the steric hindrance of the active site due to the coupled alkyl chain or by the coupling of the hydrophobic group to the active site. Further, the boundary between the hydrophobic site and the hydrophilic site is not clear, and it would be very difficult to introduce the hydrophobic group in a uniformly aligned manner into the surface of vesicle.

A dendritic sphere (dendrimer) has a large number of functional groups at its branched ends, and a plurality of functional molecules can be coupled thereto in conformity with the number of generation (a general review is disclosed by e.g., J. I. R. Moors and F. Vogtle, Angew. Chem. Int. Ed. Engl., 33, 2413, 1994). A dendrimer which is constituted from amino acids can be easily obtained by means of ordinary peptide-synthesizing method, and is excellent in both biodegradability and biocompatibility. A dendrimer constituted by lysine is first reported by R. G. Denkenwalter, et al (U.S. Pat. No. 4,289,872) (issued on Sep. 15, 1981). Since then, a synthesizing method by way of solid-phase peptide synthesis has been established (J. P. Tam et al., Proc. Natl. Acad. Sci., USA, 85, 5409, 1988), wherein a derivative thereof where a bioactive peptide or a saccharide is coupled to the branched terminal amino group is reported. An amphiphilic compound wherein polyoxyethylene is coupled to the core portion of hydrophobic dendron is already reported and is now studied on the utilization thereof as a novel functional material (I. Gitsov et al., Angew. Chem. Int. Ed. Engle., 31, 1200, 1992, T. M. Chapman et. al., J. Am. Chem. Soc., 116, 11195, 1994). Recently, an amphiphilic dendrimer wherein a plurality of hydrophobic groups are coupled to the branched terminals (A. P. H. J. Schenning et al., J. Am. Chem. Soc., 120, 8199, 1998) or a dendrimer having protein coupled thereto (P. Singh, Bioconjugate Chem., 9, 54, 1998) are reported.

An object of the present invention is to provide a novel amphiphilic compound which is capable of stably fixing a water-soluble polymer onto a surface structure by taking advantage of intermolecular interaction, thereby enabling the water-soluble polymer to be carried thereon without giving any damage to the function thereof.

BRIEF SUMMARY OF THE INVENTION

As a result of intensive studies made by the present inventors under the aforementioned circumstances and by taking a hint from the recent reports related to the dendrimer, it has been succeeded to design and synthesize an amphiphilic compound wherein a large number of hydrophobic group are introduced into the terminals of branches of dendritic branch structure (dendron) constituting, as a constituent unit, a dendrimer, and at the same time, a hydrophilic group is coupled to the sole substituent group existing at the core of dendrimer. In this case, the balance between the hydrophobic site and the hydrophilic site can be optionally controlled by adjusting the generation number of branching of dendron. Further, it has been also succeeded in introducing protein, through a single point bonding, into the terminal of the hydrophilic group, thereby accomplishing the present invention.

Namely, according to the present invention, there is provided an amphiphilic compound having a dendritic branch structure represented by the following general formula (I):

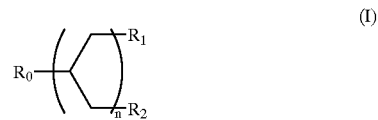

where $R_0$ is a hydrophilic group; $R_1$ and $R_2$ are independently a hydrophobic group; and n is an integer of 1 to 4. The amphiphilic compound represented by the general formula (I) is selected from the group consisting of an amphiphilic compound having a dendritic branch structure represented by the following formula (G), an amphiphilic compound having a dendritic branch structure represented by the following formula (H), and an amphiphilic compound having a dendritic branch structure represented by the following formula (J).

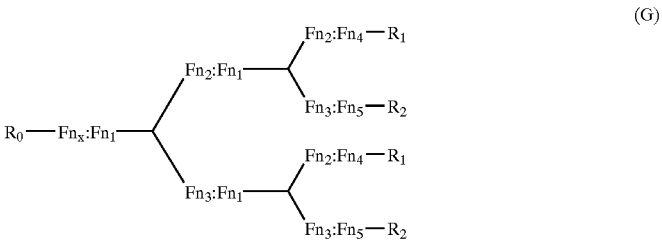

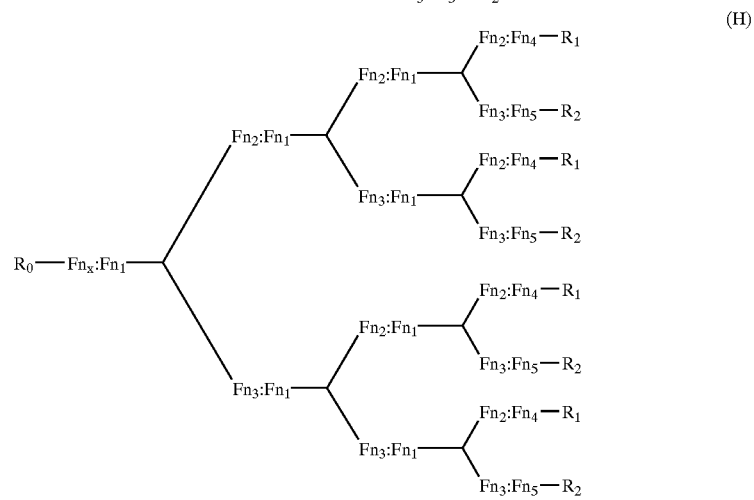

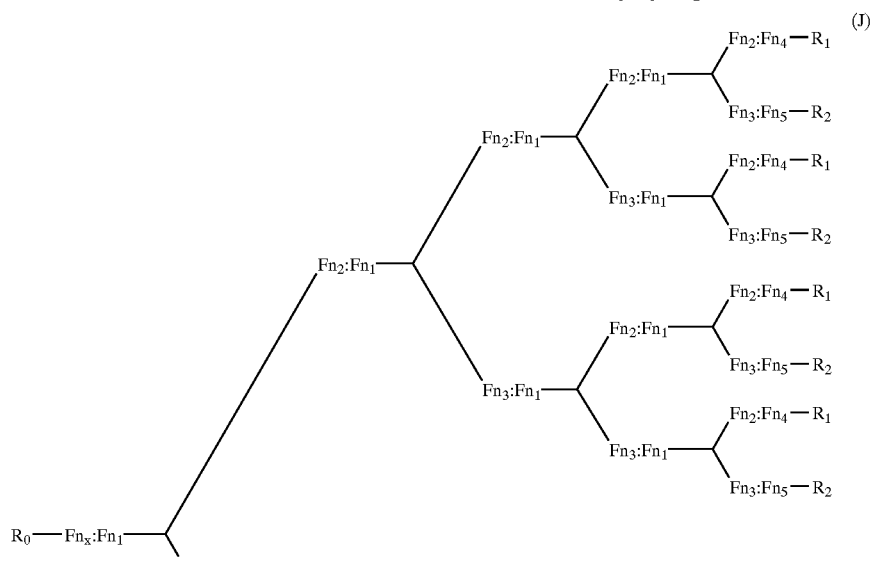

-continued

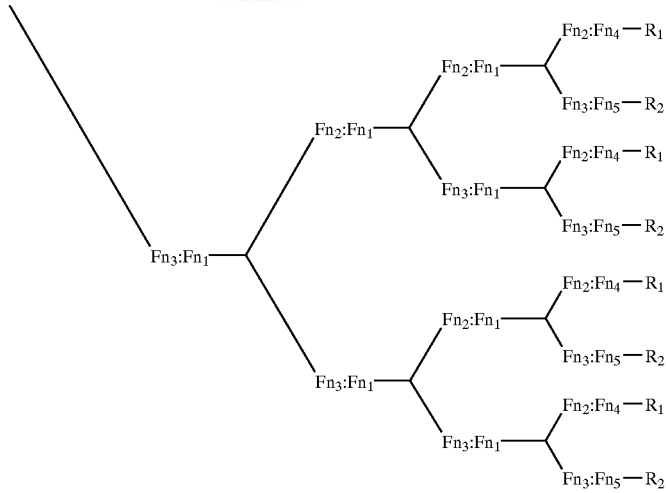

In the above formulas (G), (H) and (J), $Fn_x$, $Fn_1$, $Fn_2$, $Fn_3$, $Fn_4$ and $Fn_5$ respectively represents a functional reactive group, each of which is bonded to a neighboring functional reactive group. $R_0$, $R_1$ and $R_2$ are as defined above.

According to a preferable embodiment of the present invention, there is also provided an amphiphilic compound having a dendritic branch structure represented by the following general formula (II):

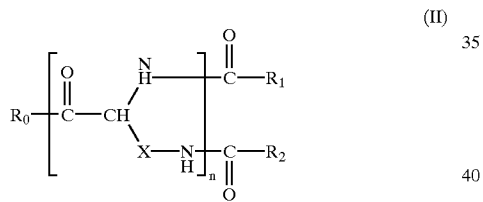
(II)

where $R_0$ is a hydrophilic group; X is $-(CH_2)_4-$ or $-(CH_2)_p-CO-$ (wherein p is 1 or 2); $R_1$ and $R_2$ are independently a hydrophobic group; and n is an integer of 1 to 4. The amphiphilic compound represented by the general formula (II) is selected from the group consisting of an amphiphilic compound having a dendritic branch structure represented by the following formula (II-1), an amphiphilic compound having a dendritic branch structure represented by the following formula (II-2), an amphiphilic compound having a dendritic branch structure represented by the following formula (II-3) and an amphiphilic compound having a dendritic branch structure represented by the following formula (II-4).

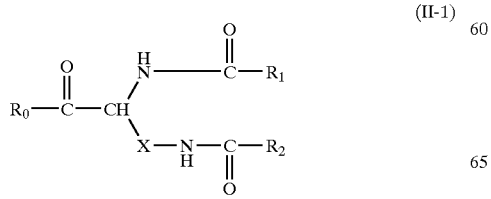
(II-1)

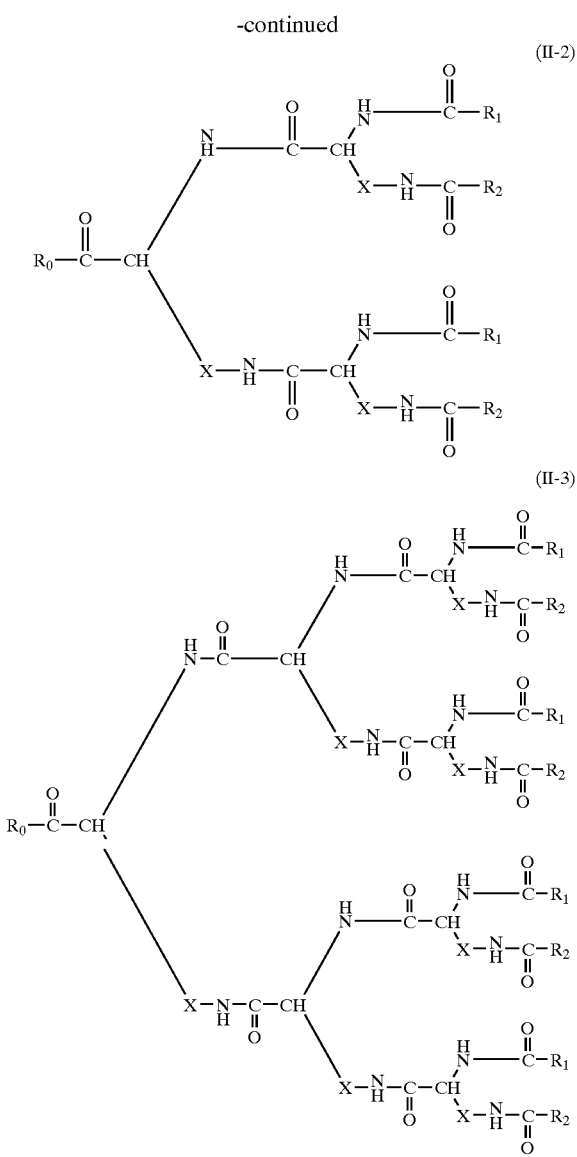

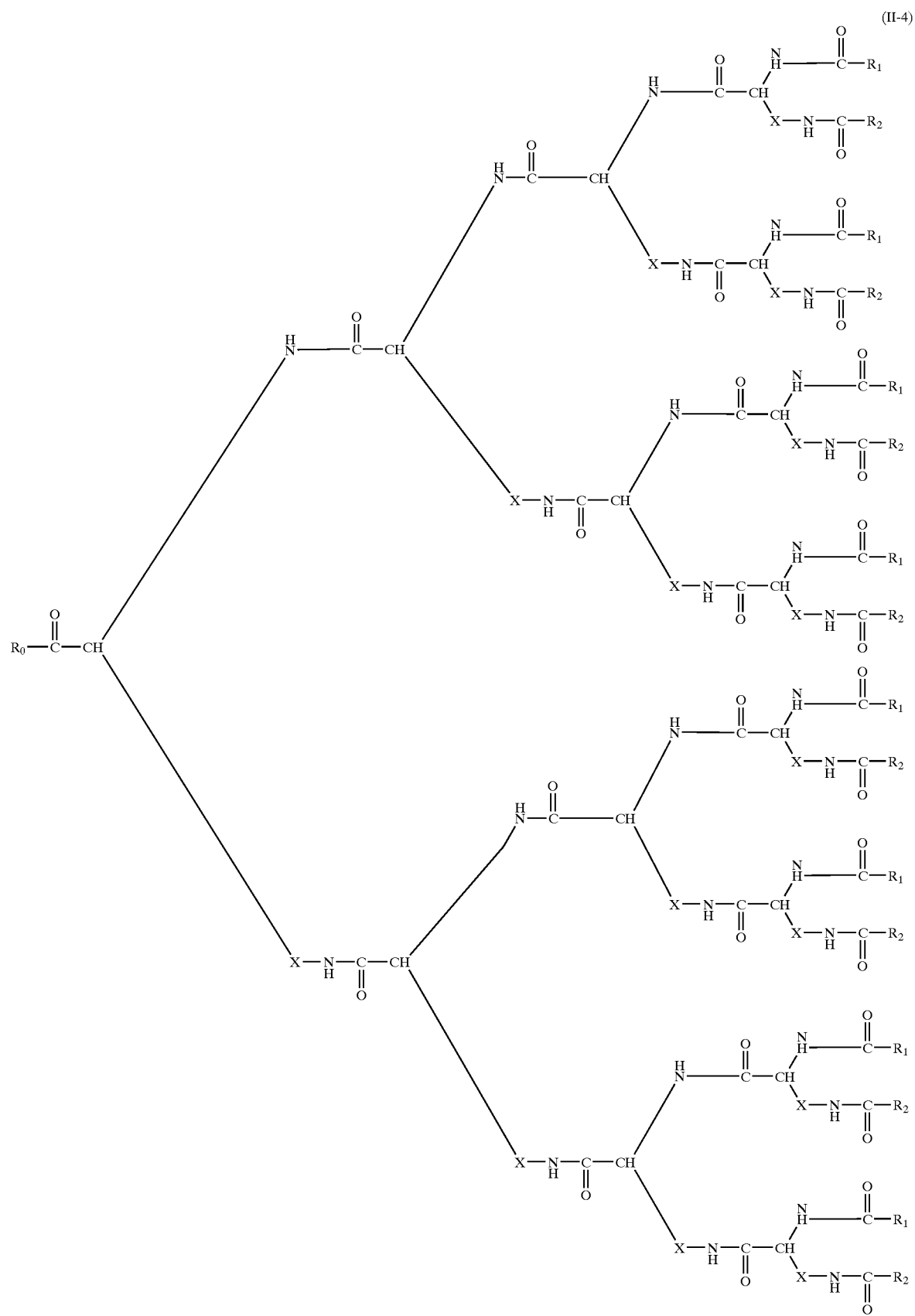

According to a second preferable embodiment of the present invention, there is also provided an amphiphilic compound having a dendritic branch structure represented by the following general formula (III):

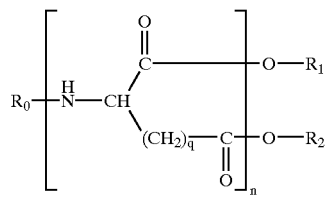
(III)

where $R_0$ is a hydrophilic group; $R_1$ and $R_2$ are independently a hydrophobic group; n is an integer of 1 to 4 and q is 1 or 2. The amphiphilic compound represented by the general formula (III) is selected from the group consisting of an amphiphilic compound having a dendritic branch structure represented by the following formula (III-1), an amphiphilic compound having a dendritic branch structure represented by the following formula (III-2), an amphiphilic compound having a dendritic branch structure represented by the following formula (III-3) and an amphiphilic compound having a dendritic branch structure represented by the following formula (III-4).

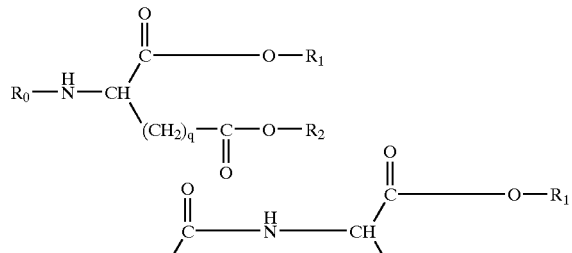
(III-1)

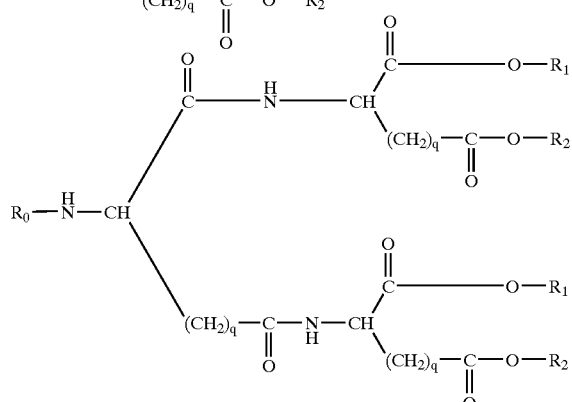
(III-2)

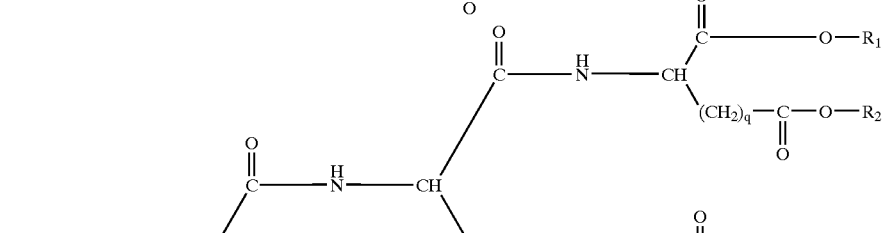
(III-3)

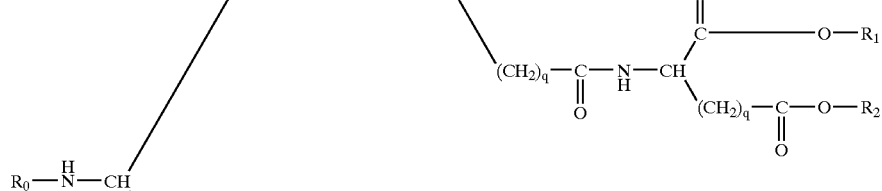

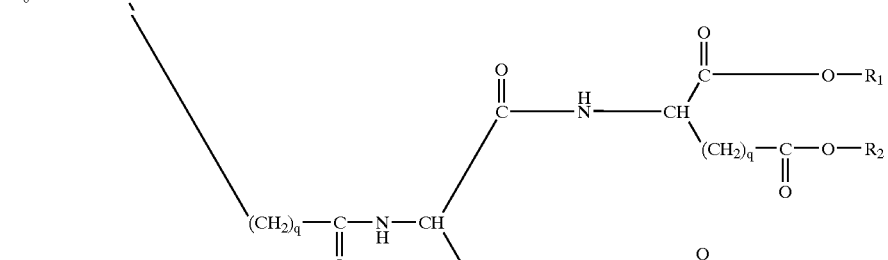

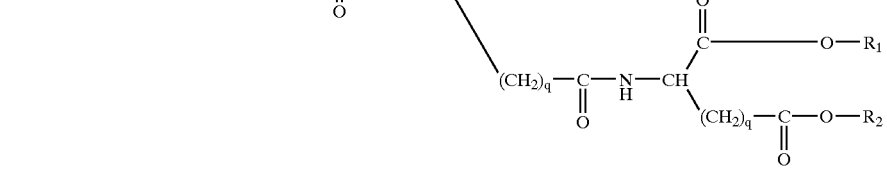

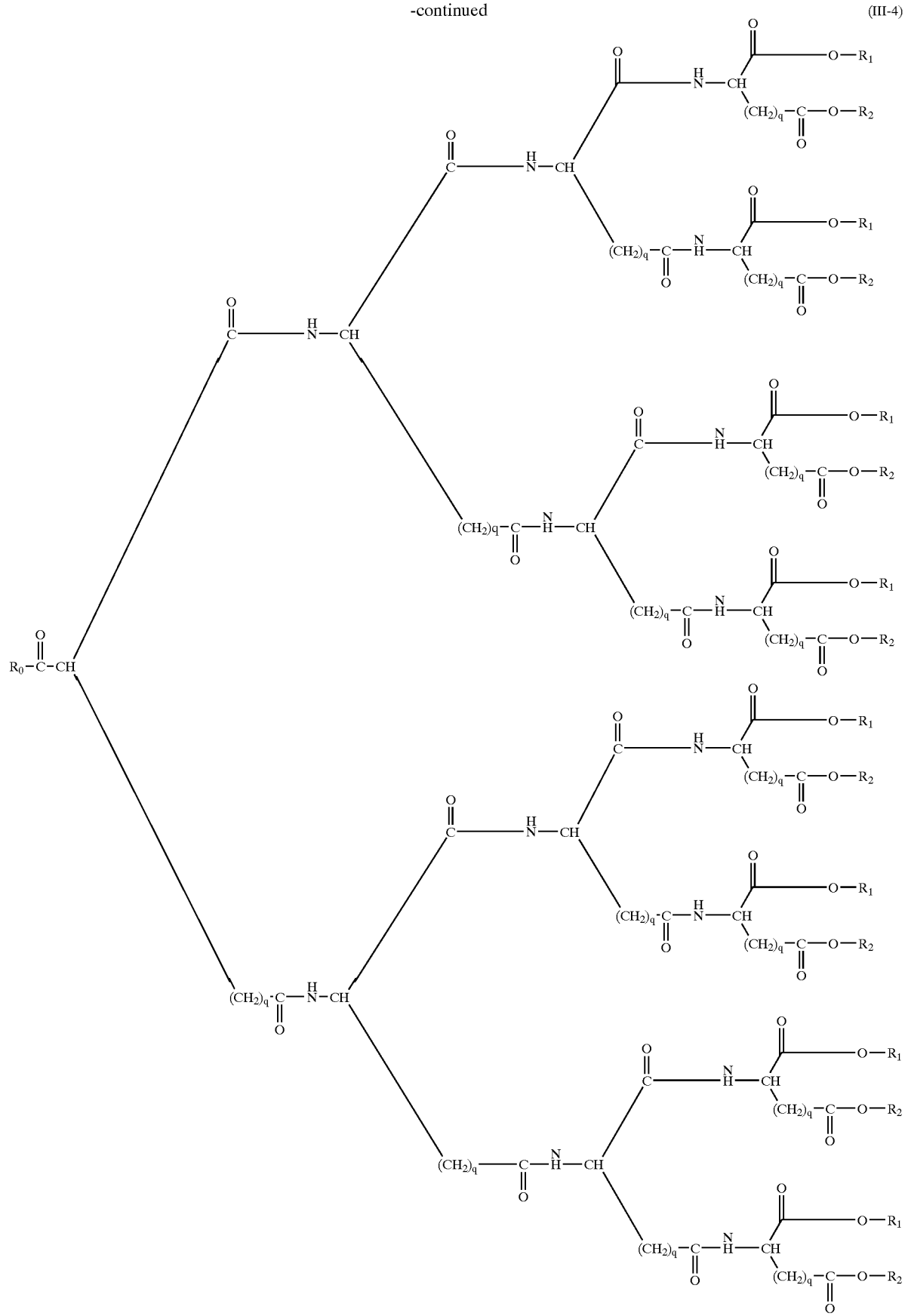

In the present invention, n should preferably be an integer of 2 or more.

In the present invention, each of $R_1$ and $R_2$ should preferably be an alkyl group, in particular, an alkyl group having 1 to 30 carbon atoms.

Further, in the present invention, $R_0$ should preferably be oligo-oxyethylene derivatives, poly- or oligo-saccharide derivatives, or poly- or oligo-peptides.

Further, in the present invention, $R_0$ may be represented by a formula: $R-(OCH_2CH_2)_mCH_2NH-$ or $R-(OCH_2CH_2)_mOCH_2C(O)NHCH_2CH_2NH-$ (wherein R is $H-$, $CH_3-$, $CH_3C(O)-$, $HOOCCH_2-$, $H_2NCH_2CH_2NHC(O)CH_2-$ or poly- or oligo-peptides; and m is an integer of 1 to 3000).

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

The amphiphilic compound having a dendritic branch structure according to the present invention can be obtained by reacting a dendron having, at the branched terminals thereof, a reactive functional group such as amino group, carboxyl group or hydroxyl group, and, at the core portion thereof, a reactive functional group such as amino group, carboxyl group, hydroxyl group, with a source of the hydrophobic groups ($R_1$ and $R_2$) as well as with a source of the hydrophilic group ($R_0$). The generation number of branching in the dendron should preferably be in the range of 1 to 5. If the dendron is to be employed as a biocompatible material, the dendron moiety should preferably be constituted by amino acids. However, the dendron moiety may not be confined to amino acids. Among amino acids, a more preferable example is a trifunctional amino acid having one reactive functional group at the core site thereof and one reactive functional group at each of a couple of branched terminals. Specific examples of such a trifunctional amino acid include lysine, asparagine, glutamine, aspartic acid, glutamic acid, serine, threonine, tyrosine, etc. Among these trifunctional amino acids, a most preferable example is a trifunctional amino acid having a first reactive functional group at the core site thereof and the same second reactive functional group at each of a couple of branched terminals (e.g. lysine having one terminal carboxyl group and a couple of terminal amino groups; or aspartic acid and glutamic acid each having one terminal amino group and a couple of terminal carboxyl group). Lysine is especially preferable among them.

The hydrophobic groups ($R_1$ and $R_2$) to be employed in the present invention may be of any kinds as long as they are capable of being introduced into the branched terminals of dendron by way of covalent bond. These hydrophobic groups may be the same with or different from each other. As specific examples of such a hydrophobic group, it is possible to employ aliphatic hydrocarbons (preferably, alkyl group), sterols, isoprenoids, and synthetic oligomer or polymer (styrene, hydrophobic peptide, etc.). For the purpose of strictly adjusting the balance between the hydrophobic site and the hydrophilic site, the employment of aliphatic hydrocarbon groups is preferable. Especially, a linear or branched hydrophobic group having 1 to 30 carbon atoms, particularly hydrocarbon group (especially, alkyl group) can be preferably employed. As for the source of such hydrocarbon groups, it is possible to employ those having amino group, carboxyl group or hydroxyl group. When this hydrophobic group includes an unsaturated bond, the number of unsaturated bond should preferably be confined to 1 to 4.

As for the source of hydrophobic group having carboxyl group, it is possible to employ fatty acids such as acetic acid, propionic acid, butyric acid, valerianic acid, iso-valerianic acid, caproic acid, enanthic acid, caprylic acid, undecanoic acid, lauric acid, tridecanoic acid, myristic acid, pentadecanoic acid, palmitic acid, margaric acid, stearic acid, nonadecanoic acid, arachic acid, behenic acid, palmitoleic acid, oleic acid, linoleic acid, linolenic acid and arachidonic acid. A branched chain having any of these acids may be also useful. The acid anhydrides of these acids and the acid chlorides thereof are also useful as well.

As for the source of the hydrophobic group having amino group, it is possible to employ a linear primary amine such as dodecyl amine, tridecyl amine, tetradecyl amine, pentadecyl amine, hexadecyl amine, heptadecyl amine, octadecyl amine, dococyl amine and oleyl amine. A branched chain having any of these amines may be also useful. Further, branched amines such as isoprenoid are also useful. As for the source having amino group, it is also possible to employ secondary amines such as N-methyl-dodecyl amine, N-methyl-tetradecyl amine, N-methyl-hexadecyl amine, N-ethyl-dodecyl amine, N-ethyl-tetradecyl amine, N-ethyl-hexadecyl amine, N-propyl-dodecyl amine, N-propyl-tetradecyl amine, N-propyl-hexadecyl amine, dioleyl amine, etc.

As for the source of the hydrophobic group having hydroxyl group, it is possible to employ a linear primary saturated alcohol such as lauryl alcohol, cetyl alcohol, stearyl alcohol, behenyl alcohol, etc. Additionally, it is also possible to employ a linear primary unsaturated alcohol, a branched primary saturated alcohol, a branched primary unsaturated alcohol, a secondary saturated alcohol or a secondary unsaturated alcohol such as 1,1-dodecenol, 1-oleyl alcohol, linolenyl alcohol, etc. Additionally, it is also possible to employ di-alkyl glycerol wherein alcohols are bonded at the 1 and 3-position or 1 and 2-position of glycerin, or di-alkyl glycerol which is constituted by primary first saturated alcohol and primary unsaturated alcohol.

As for the examples of sterols to be employed as a source of hydrophobic group, they include cholesterol, cholestanol, sitosterol and ergosterol.

There is not any restriction with regard to the hydrophilic group ($R_0$) to be employed in the present invention, so that any kinds of hydrophilic group can be employed as long as they are capable of being introduced into the core site of dendron by way of covalent bond. If the dendron is to be employed as a biocompatible material, it is preferable to employ, as unlimited examples of the hydrophilic group, r polyoxyethylene derivatives, saccharides (oligosaccharides, polysaccharides), oligo- or poly-peptides, or covalent compounds of these compounds.

As for the examples of polyoxyethylene derivatives, it is possible to employ a copolymer of ethylene glycol with polyoxyethylene 400 to 500,000 in molecular weight (weight-average molecular weight, the same hereinafter) and having, at one or both terminals thereof, a substituent group such as amino group, carboxyl group, hydroxyl group, etc. It is also possible to employ the derivatives of the above copolymer wherein the terminal substituent group is activated.

As for the examples of saccharides, it is possible to employ branched or linear oligo or polysaccharides having a polymerization degree of 2 to 400. The saccharides may be either natural or synthetic saccharides. Namely, it is possible to employ any kinds of oligosaccharide or polysaccharide as long as they are capable of being introduced into the core site of monodendron by way of covalent bond. For example, it is possible to employ oligosaccharides wherein one or more kinds of saccharide selected from glucose, fructose, xylose, galactose, mannose, glucosamine, etc. are α-bonded or β-bonded to each other, specific examples thereof being maltooligsaccharide, laminaryoligosaccharide, cellooligosaccharide, isomaltooligosaccharide, gentiooligosaccharide, nigerooligosaccharide, lactooligosaccharide, melioligosaccharide, and inulooligosaccharide. As for the examples of polysaccharides, they include starch, prulan, cellulose, mucopolysaccharides (hyaluronic acid, chondroitin, chondroitin sulfate, dermatan sulfate, ketalan sulfate, heparin, etc.), chitin, chitosan, the complex polysaccharides to be derived from the decomposed materials of polysaccharides, cells and bacteria, etc.

Specific examples of poly- or oligo-peptides include various kinds of cytokinin such as interleukin, cell transfer factor, polypeptides to be used as an extracellular matrix agent such as fibrinogen, collagen, keratin, proteoglucan, etc.; oligomers constituting part of the structure of such polypeptides; and functional polypeptides such as oxytocin, bradykinin, thyrotropin-releasing factor, enkephalin, etc. Oligopeptide generally contains 2 to 10 peptide bonds. Polypeptide generally contains at least 11 peptide bonds. By the way, poly- or oligo-peptides can be bonded to each other through a (poly)oxyethylene derivative. In that case, the (poly)oxyethylene derivative to be functioned as a spacer should preferably be polyoxyethylene having a molecular weight of 100 to 100,000. The (poly)oxyethylene derivative to be employed in the present invention is not confined to the above polyoxyethylene, but may be any kinds of (poly) oxyethylene derivative as long as they have a functional group at both terminals thereof as in the case of the aforementioned polyoxyethylene derivative.

Further, in the present invention, preferable examples of hydrophilic group ($R_0$) include R—$(OCH_2CH_2)_mCH_2NH$— or R—$(OCH_2CH_2)_mOCH_2C(O)NHCH_2CH_2NH$— (wherein R is H—, $CH_3$—, $CH_3C(O)$—, $HOOCCH_2$—, $H_2NCH_2CH_2NHC(O)CH_2$— or poly- or oligo-peptides; and m is an integer of 1 to 3000). Specific examples of poly- or oligo-peptides are the same as exemplified above.

As for the functional molecules to be bonded via the aforementioned spacer to the dendron, they include, other than poly- or oligo-peptide, the fragments thereof, antibody, antigen, peptide, stroma, enzyme, saccharide, etc.

Next, a typical method for synthesizing an amphiphilic compound having a branch structure and represented by any one of the general formulas (I) to (III) where n=1 according to the present invention will be explained with reference to the following synthesis route 1.

Synthesis Route 1 (Where n=1)

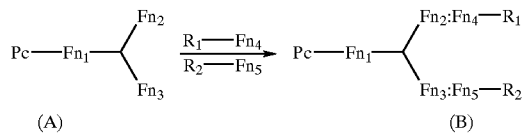

(A)    (B)

-continued

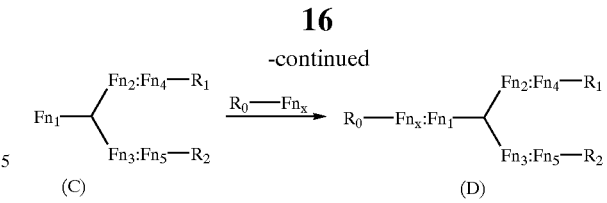

(C)    (D)

This synthesis route 1 is featured in that it starts from a trifunctional dendron having a reactive functional group $Fn_1$ (carboxyl group, etc.) at the core site thereof and reactive functional groups $Fn_2$ and $Fn_3$ (amino group, hydroxyl group, etc.) at the branched terminals thereof, respectively.

First of all, the functional group $Fn_1$ at the core site thereof is protected, if required, with a protecting group Pc according to the conventional method to obtain a compound (A). This protecting process can be performed using benzyl alcohol for instance if the functional group $Fn_1$ employed is carboxyl group. Then, this compound (A) is allowed to react with a source $R_1$-$Fn_4$ of hydrophobic group having a reactive functional group $Fn_4$ at a terminal thereof (for example, fatty acid) as well as with a source $R_2$-$Fn_5$ of hydrophobic group having a reactive functional group $Fn_5$ at a terminal thereof (for example, fatty acid). Of course, these functional groups are selected such that the functional groups $Fn_2$ and $Fn_4$ are capable of reacting with each other so as to form a covalent bond such as amid bond, ester bond, etc., and likewise, the functional groups $Fn_3$ and $Fn_5$ are capable of reacting with each other so as to form a covalent bond such as amid bond, ester bond, etc. As a result, a compound (B) is obtained. Thereafter, this compound (B) is deprotected according to the conventional method to thereby convert it into a compound (C), which is then allowed to react with a source $R_0$-$Fn_x$ of hydrophilic group having a reactive functional group $Fn_x$ at a terminal thereof to obtain a compound (D) where n=1. In the case where the source of hydrophilic group is provided at the opposite terminals thereof with a reactive functional group, this compound (D) can be further reacted with a functional polymer such as protein.

Alternatively, the compound (D) can be synthesized also by a different process wherein the functional groups at the opposite branched terminals of the starting dendron are protected in advance if required, and after finishing the introduction of a hydrophilic group into the functional groups of core site, the opposite branched terminals of the compound thus obtained are deprotected as required, which is followed by the reaction with a source of hydrophobic group in the same manner as described above.

Next, a typical method for synthesizing an amphiphilic compound having a branch structure and represented by any one of the general formulas (I) to (III) where n=2 according to the present invention will be explained with reference to the following synthesis route 2.

Synthesis Route 2 (Where n=2)

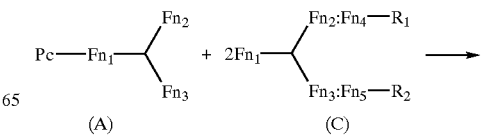

(A)    (C)

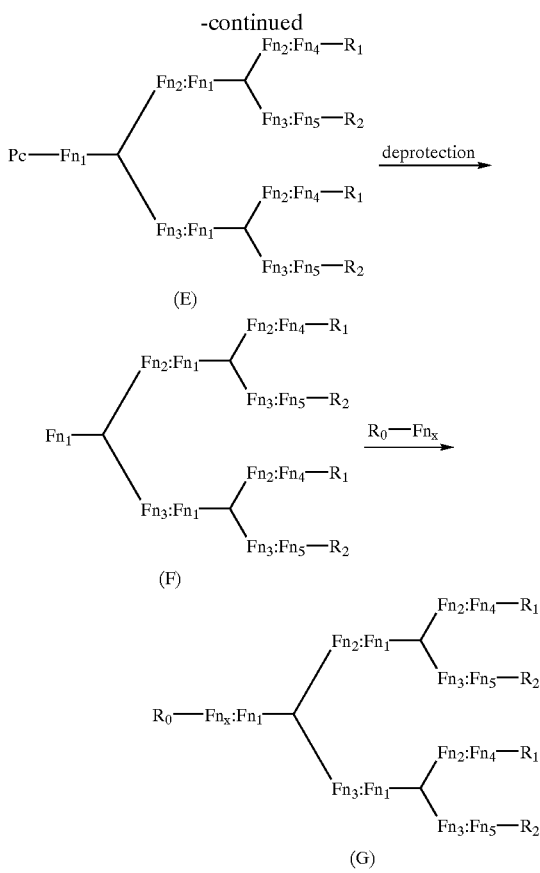

(E)

(F)

(G)

In this route, one molar quantity of the compound (A) of the above synthesis route 1 is allowed to react with two molar quantity of the compound (C) to synthesize a compound (E). Thereafter, this compound (E) is deprotected to thereby convert it into a compound (F), which is then allowed to react with a source $R_0$-$Fn_x$ of hydrophilic group to obtain a compound (G) where n=2.

Alternatively, the compound (G) can be synthesized also by a different process wherein the functional groups at the opposite branched terminals of the starting dendron are protected in advance if required, and after finishing the introduction of a hydrophilic group R0 into the functional groups of core site, the opposite branched terminals of the compound thus obtained are deprotected as required, which is followed by a process wherein one molar quantity of the resultant compound is allowed to react with two molar if quantity of the compound (C) in the same manner as described above to thereby obtain the compound (G).

An amphiphilic compound represented by any one of the general formulas (I) to (III) where n=3 can be synthesized by a process wherein one molar quantity of the above compound (A) is allowed to react with two molar quantity of the compound (F) to synthesize a compound (hereinafter referred to as a compound (pre-H)). Thereafter, this compound (pre-H) is subjected to the deprotection and to the introduction of a hydrophilic group in the same manner as explained above to thereby synthesize the amphiphilic compounds, which can be represented by the aforementioned formulas (H), (II-3) and (III-3).

An amphiphilic compound represented by any one of the general formulas (I) to (III) where n=4 can be synthesized by a process wherein one molar quantity of the above compound (A) is allowed to react with two molar quantity of the compound (pre-H) to synthesize a compound. Thereafter, the compound thus obtained is subjected to the deprotection and to the introduction of a hydrophilic group in the same manner as explained above to thereby synthesize the amphiphilic compounds, which can be represented by the aforementioned formulas (J), (II-4) and (III-4).

As explained above, when lysine, glutamine, aspartic acid, etc. are employed as a starting dendron, amphiphilic compounds corresponding to the general formula (II) can be obtained, whereas when aspartic acid, glutamic acid, etc. are employed as a starting dendron, amphiphilic compounds corresponding to the general formula (III) can be obtained.

The present invention will be further explained with reference to the following examples which are not intended to limit the present invention whatsoever. By the way the structures of the compounds (derivatives) in the following examples will be summarized at the end of description.

EXAMPLE 1

In this example, a compound (n=1) having polyoxyethylene at the hydrophilic site thereof with lysine being employed as a spacer, and a couple of alkyl groups at the hydrophobic site thereof was synthesized.

(A) First of all, a protecting group was introduced into the carboxyl group of lysine as follows. Namely, L-lysine (5.1 g, 35.2 mmol), p-toluenesulfonic acid (14.7 g, 77.3 mmol) and benzyl alcohol (14.0 g, 124.1 mmol) were dissolved in benzene (30 mL) employed as a solvent. The resultant solution was refluxed for 6 hours at 100° C. while removing water produced. After the solvent was removed in vacuum, the residue was subjected to the reprecipitation thereof which was repeated three times using diethyl ether to refine the product. This refined product was recrystallized from a mixed solvent of methanol/diethyl ether at 4° C., and then, subjected to filtration and desiccation to obtain, as a white solid matter, a lysine derivative 1 having carboxyl group protected with benzyl ester (18.0 g, yield: 88%).

<Results of Analysis of the Lysine Derivative 1>

Thin-layer chromatography (silica gel plate, chloroform/methanol (4/1) (vol./vol.): $R_f$: 0.2 (monospot))

Infrared spectrum ($cm^{-1}$): 3034; 2952 [$v_{N-H}$ ($NH_3^+$)]; 1749 [$v_{C=O}$ (ester)]; 1600 [$\delta_{N-H}$ ($NH_3^+$)].

$^1$H-NMR spectrum (DMSO-d6, 500 MHz, δ (ppm)): 1.28, 1.40 (m, 2H, Lys β-$CH_2$); 1.51 (m, 2H, Lys v-$CH_2$); 1.80 (m, 2H, Lys δ-$CH_2$); 2.29 (s, 6H, —$CH_3$); 2.70 (m, 2H, Lys ε-$CH_2$); 4.09 (s, 1H, Lys α-$CH_2$); 5.25 (s, 2H, —$CH_2$—); 7.12, 7.48 (8H, p-Tos-aroma.); 7.35–7.42 (5H, aroma.); 7.67, 8.38 (s, 6H, —$NH_3^+$).

(B) An alkyl group was introduced as a hydrophobic group into the amino groups of the lysine derivative as follows. Namely, palmitic acid (3.2 g, 12.4 mmol) and N,N'-dicyclohexyl carbodiimide (2.6 g, 12.4 mmol) were dissolved in chloroform employed as a solvent. The resultant solution was stirred for 30 minutes at 25° C. to obtain a mixed solution, to which the lysine derivative 1 (3.0 g, 5.12 mmol) and triethyl amine (1.2 g, 11.4 mmol) were added. This reaction mixture was stirred for 12 hours at 4° C. and then, subjected to the filtration thereof using a glass filter (G4). Thereafter, the solvent was removed in vacuum, and the residue was redissolved in chloroform (100 mL) and washed three times using a saturated aqueous solution of sodium carbonate and further washed three times using water. After the chloroform phase was dehydrated by making use of anhydrous sodium sulfate, the solvent was removed in vacuum. The resultant product was recrystallized from methanol (200 mL) at 4° C., and then, subjected to filtration and desiccation to obtain, as a white solid matter, a lysine derivative 2 having an alkyl group bonded via amid-bond to each of amino group (2.9 g, yield: 79%).

<Results of Analysis of the Lysine Derivative 2>

Thin-layer chromatography (silica gel plate, chloroform/methanol (4/1) (vol./vol.): $R_f$: 0.53 (monospot))

Infrared spectrum (cm$^{-1}$): 3311 ($v_{N-H}$ (amide)); 1748 ($v_{C=O}$ (ester)); 1640 ($v_{C=O}$ (amide)); 1553 ($\delta_{N-H}$ (amide)), $^1$H-NMR spectrum (CDCl$_3$, 500 MHz, δ (ppm)): 0.85 (t, 6H, —CH$_3$); 1.23 (s, 50H, —CH$_2$—CH$_2$—, Lys v-CH$_2$); 1.46 (m, 2H, Lys δ-CH$_2$); 1.58 (m, 4H, —N—CO—C—CH$_2$—); 1.66, 1.82 (m, 2H, Lys β-CH$_2$); 2.12, 2.20 (t, 4H, —N—CO—CH$_2$—); 3.16 (m, 2H, Lys ε-CH$_2$); 4.58 (m, 1H, Lys α-CH$_2$); 5.13 (m, 2H, —CH$_2$—); 5.65 (br, 1H, —NH—CO—); 6.16 (d, 1H, —NH—CO—); 6.16 (d, 1H, —NH—CO—); 7.29–7.37 (5H, aroma.).

(C) The lysine derivative 2 (1.52 g, 2.13 mmol) was dissolved in a mixed solvent consisting of chloroform/methanol (10/7) (vol./vol.). To this resultant solution was added a 1N aqueous solution of sodium hydroxide to obtain a reaction mixture. After this reaction mixture was stirred for 4 hours at 25° C., a 1N aqueous solution of hydrochloric acid was added thereto (until pH became 3.0). Then, the solvent was removed in vacuum, and the residue was washed with water and methanol. Thereafter, the product thus obtained was dried to obtain, as a white solid matter, a dipalmitoyl lysine derivative 3 (1.3 g, yield: 98%).

<Results of Analysis of the Dipalmitoyl Lysine Derivative 3>

Thin-layer chromatography (silica gel plate, chloroform/methanol (4/1) (vol./vol.): $R_f$: 0.45 (monospot))

Infrared spectrum (cm$^{-1}$): 3305 ($v_{N-H}$ (amide)); 1721 ($v_{C=O}$ (carbonyl)); 1638 ($v_{C=O}$ (amide)); 1553 $\delta_{N-H}$ (amide)

$^1$H-NMR spectrum (DMSO-d6, 500 MHz, δ (ppm)): 0.84 (t, 6H, —CH$_3$); 1.24 (s, 50H, —CH$_2$—CH$_2$—, Lys v-CH$_2$); 1.36 (m, 2H, Lys δ-CH$_2$); 1.47 (m, 4H, —N—CO—C—CH$_2$—); 1.55, 1.67 (m, 2H, Lys β-CH$_2$); 2.02, 2.09 (t, 4H, —N—CO—CH$_2$—); 2.99 (m, 2H, Lys ε-CH$_2$); 4.14 (m, 1H, Lys α-CH$_2$); 7.55 (br, 1H, —NH—CO—); 7.78 (d, 1H, —NH—CO—); 12.23 (br, 1H, —COOH—).

MS (FAB): Calculated value for C$_{38}$H$_{74}$N$_2$O$_4$: 623.0; Found value therefor: 623.5 (M$^+$H)$^+$.

Elemental analysis for C$_{38}$H$_{74}$N$_2$O$_4$: Calculated value: C, 73.26; H, 11.97; N, 4.50; Found value: C, 72.39; H, 12.43; N, 4.74.

(D) The same procedures as those of above paragraphs (B) and (C) were repeated except that myristic acid and stearic acid were used instead of the palmitic acid to thereby obtain dialkyl lysine derivatives (dimyristoyl lysine derivative 4 and distearoyl lysine derivative 5), each as a white solid matter.

<Results of Analysis of the Dimyristoyl Lysine Derivative 4>

Thin-layer chromatography (silica gel plate, chloroform/methanol (4/1) (vol./vol.): $R_f$: 0.40 (monospot))

IR (cm$^{-1}$): 3305 ($v_{N-H}$ (amide)); 1721 ($v_{C=O}$ (carbonyl)); 1638 ($v_{C=O}$ (amide)); 1553 ($\delta_{N-H}$ (amide)).

$^1$H-NMR spectrum (DMSO, 500 MHz, δ (ppm)): 0.84 (t, 6H, —CH$_3$); 1.24 (s, 42H, —CH$_2$—CH$_2$—, Lys v-CH$_2$); 1.36 (m, 2H, Lys δ-CH$_2$); 1.47 (m, 4H, —N—CO—C—CH$_2$—); 1.55, 1.67 (m, 2H, Lys β-CH$_2$); 2.02, 2.09 (t, 4H, —N—CO—CH$_2$—); 2.99 (m, 2H, Lys ε-CH$_2$); 4.14 (m, 1H, Lys α-CH$_2$); 7.55 (br, 1H, —NH—CO—); 7.78 (d, 1H, —NH—CO—); 12.23 (br, 1H, —COOH—).

<Results of Analysis of the Distearoyl Lysine Derivative 5>

Thin-layer chromatography (silica gel plate, chloroform/methanol (4/1) (vol./vol.): $R_f$: 0.53 (monospot))

IR (cm$^{-1}$): 3305 ($v_{N-H}$ (amide)); 1721 ($v_{C=O}$ (carbonyl)); 1638 ($v_{C=O}$ (amide)); 1553 ($\delta_{N-H}$ (amide)).

$^1$H -NMR spectrum (CDCl$_3$, 500 MHz, δ (ppm)): 0.87 (t, 6H, —CH$_3$); 1.24 (s, 56H, —CH$_2$—CH$_2$—); 1.36 (m, 2H, Lys δ-CH$_2$); 1.48 (m, 2H, Lys β-CH$_2$); 1.59 (m, 4H, —N—CO—C—CH$_2$—); 1.74, 1.86 (m, 2H, Lys β-CH$_2$); 2.15, 2.23 (t, 4H, —N—CO—CH$_2$—); 3.17, 3.29 (m, 2H, Lys ε-CH$_2$—CH$_2$); 4.40 (m, 1H, Lys α-CH$_2$); 5.88 (br, 1H, —NH—CO—); 6.75 (d, 1H, —NH—CO—); 12.23 (br, 1H, —COOH—).

(E) The dipalmitoyl lysine derivative 3 was bonded to polyoxyethylene as follows. Namely, the dipalmitoyl lysine derivative 3 (125 mg, 0.2 mmol) and DCC (41 mg, 0.2 mmol) were dissolved in chloroform to obtain a solution, which was subsequently stirred for one hour at 4° C. Then, the resultant solution was dropped into a solution of monomethoxy aminopolyoxyethylene (500 mg, 0.1 mmol) having a molecular weight of 5,000 and dimethylaminopyridine (24 mg, 0.2 mmol) in chloroform to obtain a reaction mixture. After being stirred for 6 hours at 25° C., this reaction mixture was filtered by making use of a glass filter (G4) to obtain a filtrate, which was then dropped into diethyl ether. Then, the precipitate was recovered by means of filtration and dried, and by making use of a silica gel column (solvent: chloroform/methanol=6/1 (vol./vol.)), an amphiphilic compound 6 of the present invention was isolated (500 mg, yield: 88%).

<Results of Analysis of the Derivative 6>

Thin-layer chromatography (silica gel plate, chloroform/methanol (4/1) (vol./vol.): $R_f$: 0.73 (monospot))

IR (cm$^{-1}$): 3294 ($v_{N-H}$ (amide)); 1634 ($v_{C=O}$ (amide)); 1553 ($\delta_{N-H}$ (amide)).

$^1$H-NMR spectrum (CDCl$_3$, 500 MHz, δ (ppm)): 0.88 (t, 6H, —CH$_3$); 1.25 (s, 50H, —CH$_2$—CH$_2$—, Lys δ-CH$_2$); 1.32 (m, 2H, Lys δ-CH$_2$); 1.63–1.80 (8H, —CH$_2$—C—N, —N—CO—C—CH$_2$—, Lys β—CH$_2$); 2.27, 2.38 (t, 4H, —N—CO—CH$_2$—); 3.29 (m, 2H, Lys ε-CH$_2$); 3.38 (3H, —O—CH$_3$); 3.43 (2H, —CH$_2$—NH—); 3.66 (PEG); 4.39 (m, 1H, Lys α-CH$_2$).

$^{13}$C-NMR spectrum (CDCl$_3$, 500 MHz, δ (ppm)): 14.12; 22.68; 25.74; 28.75; 29.34; 29.53; 29.65; 31.92; 36.35; 38.13; 59.02; 70.44; 71.95.

Elemental analysis for C$_{268}$H$_{535}$N$_3$O$_{118}$: Calculated value: C, 56.59; H, 9.48; N, 0.739; O, 33.19; Found value: C, 56.88; H, 9.87; N, 1.07; O, 32.18.

(F) The procedures similar to those of above paragraph (E) were repeated except that a combination of the molecular weight of polyoxyethylene and hydrophobic group was varied to thereby obtain the following compounds. Although the details of the analysis are omitted herein, the area ratio between the terminal methyl proton A of alkyl chain (0.88 ppm, 3H× the number of alkyl chain) which is a criterion of the number of alkyl chain and the terminal methyl proton B of polyoxyethylene (3.38 ppm, 3H), which was measured by means of $^1$H-NMR spectrum, is shown below.

The area ratio between polyoxyethylene (molecular weight: 5,000) and dimyristoyl lysine derivative 4 (A/B) was 2.0; the area ratio between polyoxyethylene (molecular weight: 5,000) and distearoyl lysine derivative 5 (A/B) was 2.0; the area ratio between polyoxyethylene (molecular weight: 12,000) and distearoyl lysine derivative 5 (A/B) was 2.0; and the area ratio between polyoxyethylene (molecular weight: 20,000) and distearoyl lysine derivative 5 (A/B) was 1.9.

EXAMPLE 2

In this example, a compound (n=2) having four chains of alkyl groups was synthesized as follows.

(A) First of all, dipalmitoyl lysine derivative 3 (600 mg, 0.96 mmol) and DCC (200 mg, 0.96 mmol) were dissolved in chloroform to obtain a solution, which was stirred for one hour at 4° C. Then, the resultant solution was dropped into a solution of the lysine derivative 1 (278 mg, 0.48 mmol) and dimethylaminopyridine (120 mg, 0.96 mmol) in chloroform to obtain a reaction mixture. After being stirred for 6 hours at 25° C., this reaction mixture was filtered by making use of a glass filter (G4) to obtain a filtrate, which was then dropped into diethyl ether. Then, the precipitate was recovered by means of filtration and dried, and by making use of a silica gel column (solvent: chloroform/methanol=6/1 (vol./vol.)), the product compound was refined. This compound was then dissolved in chloroform and allowed to contact with hydrogen gas under the presence of palladium carbon to thereby remove the protecting group thereof through the reduction of the compound. This reaction mixture was then filtered and recrystallized from chloroform at 4° C. to thereby isolate tetrapalmitoyl lysine 7 (358 mg, yield: 55%).

<Results of Analysis of the Tetrapalmitoyl Lysine 7>

Thin-layer chromatography (silica gel plate, chloroform/methanol (4/1) (vol./vol.): $R_f$: 0.45 (monospot))

IR (cm$^{-1}$): 3305 ($v_{N-H}$ (amide)); 1636 ($v_{C=O}$ (amide)); 1555 ($\delta_{N-H}$ (amide)).

$^1$H-NMR spectrum (CDCl$_3$, 500 MHz, δ (ppm)): 0.86 (t, 12H, —CH$_3$); 1.24 (s, 102H, —CH$_2$—CH$_2$—, Lys δ-CH$_2$); 1.51 (br, 6H, Lys δ-CH$_2$); 1.60 (8H, —N—CO—C—CH$_2$—); 1.82 (br, 6H, Lys β-CH$_2$); 2.15 (br, 8H, —N—CO—C—CH$_2$—); 3.22 (br, 6H, Lys ε-CH$_2$); 4.43 (br, 3H, Lys α-CH$_2$); 5.70–6.75 (br, 6H, —NH—CO—, Lys α-CH$_2$).

(B) The same procedures as those of above paragraphs (A) were repeated except that dimyristoyl lysine derivative 4 and distearoyl lysine derivative 5 were substituted for the dipalmitoyl lysine derivative 3 to thereby obtain tetraalkyl lysine derivatives (tetramyristoyl lysine derivative 8 and tetrastearoyl lysine derivative 9), each as a white solid matter.

<Results of Analysis of the Tetramyristoyl Lysine Derivative 8>

Thin-layer chromatography (silica gel plate, chloroform/methanol (4/1) (vol./vol.): $R_f$: 0.42 (monospot))

IR (cm$^{-1}$): 3305 ($v_{N-H}$ (amide)); 1636 ($v_{C=O}$ (amide)); 1555 ($\delta_{N-H}$ (amide)).

$^1$H-NMR spectrum (CDCl$_3$, 500 MHz, δ (ppm)): 0.86 (t, 12H, —CH$_3$); 1.24 (s, 86H, —CH$_2$—CH$_2$—, Lys v-CH$_2$); 1.51 (br, 6H, Lys δ-CH$_2$); 1.60 (8H, —N—CO—C—CH$_2$—); 1.82 (br, 6H, Lys β-CH$_2$); 2.15 (br, 8H, —N—CO—CH$_2$—); 3.22 (br, 6H, Lys ε-CH$_2$); 4.43 (br, 3H, Lys α-CH$_2$); 5.70–6.75 (br, 6H, —NH—CO—, Lys α-CH$_2$)

<Results of Analysis of the Tetrastearoyl Lysine Derivative 9>

Thin-layer chromatography (silica gel plate, chloroform/methanol (4/1) (vol./vol.): $R_f$: 0.48 (monospot))

IR (cm$^{-1}$): 3305 ($v_{N-H}$ (amide)); 1636 ($v_{C=O}$ (amide)); 1555 ($\delta_{N-H}$ (amide)).

$^1$H-NMR spectrum (CDCl$_3$, 500 MHz, δ (ppm)): 0.86 (t, 12H, —CH$_3$); 1.24 (s, 118H, —CH$_2$—CH$_2$—, Lys v-CH$_2$); 1.51 (br, 6H, Lys δ-CH$_2$); 1.60 (8H, —N—CO—C—CH$_2$—); 1.82 (br, 6H, Lys β-CH$_2$); 2.15 (br, 8H, —N—CO—CH$_2$—); 3.22 (br, 6H, Lys ε-CH$_2$); 4.43 (br, 3H, Lys α-CH$_2$); 5.70–6.75 (br, 6H, —NH—CO—, Lys α-CH$_2$).

(C) The tetraalkyl lysine derivative 7 was bonded to polyoxyethylene as follows. Namely, the tetraalkyl lysine derivative 7 (280 mg, 0.2 mmol) and DCC (41 mg, 0.2 mmol) were dissolved in chloroform to obtain a solution, which was subsequently stirred for one hour at 4° C. Then, the resultant solution was dropped into a solution of monomethoxy aminopolyoxyethylene (500 mg, 0.1 mmol) having a molecular weight of 5,000 and dimethylaminopyridine (24 mg, 0.2 mmol) in chloroform to obtain a reaction mixture. After being stirred for 24 hours at 25° C., this reaction mixture was filtered by making use of a glass filter (G4) to obtain a filtrate, which was then dropped into diethyl ether. Then, the precipitate was recovered by means of filtration and dried, and by making use of a silica gel column (solvent: chloroform/methanol=6/1 (vol./vol.)), an amphiphilic compound 10 of the present invention was isolated (448 mg, yield: 70%).

<Results of Analysis of the Compound 10>

Thin-layer chromatography (silica gel plate, chloroform/methanol (4/1) (vol./vol.): $R_f$: 0.78 (monospot))

IR (cm$^{-1}$): 3305 ($v_{N-H}$ (amide)); 1638 ($v_{C=O}$ (amide)); 1556 ($\delta_{N-H}$ (amide)).

$^1$H-NMR spectrum (CDCl$_3$, 500 MHz, δ (ppm)): 0.88 (t, 12H, —CH$_3$); 1.25 (s, 110H, —CH$_2$—CH$_2$—, Lys δ-CH$_2$); 1.35–1.90 (br, 22H, Lys δ-CH$_2$, —CH$_2$—C—N—, —N—CO—C—CH$_2$—, Lys β-CH$_2$); 2.00–2.45 (br, 8H, —N—CO—C—CH$_2$—); 3.30 (br, 6H, Lys ε-CH$_2$); 3.38 (s, 3H, —O—CH$_3$); 3.43 (br, 2H, —CH$_2$—NH—); 3.66 (PEG); 4.48 (br, 3H, Lys α-CH$_2$).

$^{13}$C-NMR spectrum (CDCl$_3$, 500 MHz, δ (ppm)): 14.12; 22.68; 25.79; 26.79; 29.36; 29.42; 29.59; 29.72; 31.93; 59.03; 70.58; 71.95.

(D) The procedures similar to those of above paragraph (C) were repeated except that a combination of the molecular weight of polyoxyethylene and hydrophobic group was varied to thereby obtain the following compounds. Although the details of the analysis are omitted herein, the area ratio between the terminal methyl proton A of alkyl chain (0.88 ppm, 3H× the number of alkyl chain) which is a criterion of the number of alkyl chain and the terminal methyl proton B of polyoxyethylene (3.38 ppm, 3H), which was measured by means of $^1$H-NMR spectrum, is shown below.

The area ratio between polyoxyethylene (molecular weight: 12,000) and tetrapalmitoyl lysine derivative 7 (A/B) was 3.9; the area ratio between polyoxyethylene (molecular weight: 12,000) and tetrastearoyl lysine derivative 9 (A/B) was 4.0; and the area ratio between polyoxyethylene (molecular weight: 20,000) and tetrastearoyl lysine derivative 9 (A/B) was 4.0.

EXAMPLE 3

In this example, a compound having four chains of alkyl groups was synthesized as follows.

(A) First of all, L-lysine (1.5 g, 10.3 mmol) and t-butoxycarbonyl anhydride (6.3 g, 29.0 mmol) were dissolved in a mixed solvent consisting of dioxane (20 mL), water (10 mL) and 1N NaOH (10 mL) to obtain a solution, which was stirred for 6 hours at 25° C. Then, the resultant reaction mixture was concentrated to a volume of 10 mL under a reduced pressure, and reprecipitated in hexane to refine the product. Then, this precipitated product was dissolved in water (10 mL) and filtered. Then, the filtrate was lyophilized to obtain, as a white matter, a lysine derivative 11 whose amino group was protected with t-butoxycarbonyl group (Boc) (2.64 g, yield: 74%).

<Results of Analysis of the Lysine Derivative 11>

Thin-layer chromatography (silica gel plate, chloroform/methanol (4/1) (vol./vol.): $R_f$: 0.50 (monospot))

$^1$H-NMR spectrum (CDCl$_3$, 500 MHz, δ (ppm)): 1.27–1.58 (22H, —CH$_3$, Lys ν-CH$_2$, Lys δ-CH$_2$); 1.74, 1.87 (br, 2H, Lys β-CH$_2$); 3.12 (br, 2H, Lys ε-CH$_2$); 4.29 (br, 1H, Lys α-CH$_2$); 4.63, 5.21 (br, 2H, —NH—COO—).

(B) The lysine derivative 11 (83 mg, 0.24 mmol) and DCC (50 mg, 0.24 mmol) were dissolved in chloroform to obtain a solution, which was subsequently stirred for one hour at 4° C. Then, the resultant solution was dropped into a solution of monomethoxy aminopolyoxyethylene (1.0 g, 0.2 mmol) and dimethylaminopyridine (24 mg, 0.2 mmol) in chloroform to obtain a reaction mixture. After being stirred for 6 hours at 25° C., this reaction mixture was filtered by making use of a glass filter (G4) to obtain a filtrate, which was then dropped into diethyl ether. Then, the precipitate was recovered by means of filtration and dried to obtain a compound 12 comprising polyoxyethylene, one terminal of which is bonded with lysine (0.97 g, yield: 90%).

<Results of Analysis of the Compound 12>

Thin-layer chromatography (silica gel plate, chloroform/methanol (4/1) (vol./vol.): $R_f$: 0.62 (monospot))

$^1$H-NMR spectrum (DMSO-d6, 500 MHz, δ (ppm)): 1.36 (m, 2H, Lys ν-CH$_2$); 1.44 (s, 18H, —CH$_3$); 1.49 (m, 2H, Lys δ-CH$_2$); 1.60, 1.83 (m, 2H, Lys β-CH$_2$); 1.78 (t, 2H, —CH$_2$—C—N—); 3.08 (t, 2H, —CH$_2$—N—); 3.3–3.4 (m, 2H, Lys ε-CH$_2$); 3.36 (s, 3H, —O—CH$_3$); 3.64 (PEG); 4.03 (m, 1H, Lys α-CH$_2$); 4.70, 5.30 (2H, —NH—COO—); 6.79 (1H, —NH—CO—).

(C) The compound 12 (0.5 g, 0.09 mmol) was dissolved in TFA (5 mL) to obtain a solution, which was subsequently stirred for one hour at 4° C. Then, the resultant solution was dropped into diethyl ether. Then, the precipitate was recovered by means of filtration and dried to obtain a compound 13 (0.44 g, yield: 91%).

<Results of Analysis of the Compound 13>

Thin-layer chromatography (silica gel plate, chloroform/methanol (4/1) (vol./vol.): $R_f$: 0.32 (monospot)).

$^1$H-NMR spectrum (DMSO-d6, 500 MHz, δ (ppm)): 1.60 (m, 2H, Lys ν-CH$_2$); 1.8–1.9 (m, 4H, —CH$_2$—C—N—, Lys δ-CH$_2$); 2.05 (m, 2H, Lys β-CH$_2$); 3.06 (t, 2H, —CH$_2$—N—CO—); 3.25–3.40 (m, 2H, Lys ε-CH$_2$); 3.38 (s, 3H, —O—CH$_3$); 3.65 (PEG); 4.15 (m, 1H, Lys α-CH$_2$); 7.64, 7.83, 8.41 (br, 7H, —NH—CO—, —NH$_3^+$)

(D) The dipalmitoyl lysine derivative 3 (100 mg, 0.15 mmol) and DCC (30 mg, 0.15 mmol) were dissolved in chloroform to obtain a solution, which was subsequently stirred for one hour at 25° C. Then, the resultant solution was dropped into a solution of the compound 13 obtained as mentioned above (200 mg, 0.038 mmol) and dimethylaminopyridine (4.5 mg, 0.037 mmol) in chloroform to obtain a reaction mixture. After being stirred for 6 hours at 25° C., this reaction mixture was dropped into diethyl ether. Then, the precipitate was recovered by means of filtration. Thereafter, by making use of a silica gel column (solvent: chloroform/methanol=6/1 (vol./vol.)), an amphiphilic compound 14 of the present invention was isolated (180 mg, yield: 78%).

<Results of Analysis of the Compound 14>

Thin-layer chromatography (silica gel plate, chloroform/methanol (4/1) (vol./vol.): $R_f$: 0.78 (monospot))

IR (cm$^{-1}$): 3305 ($\nu_{N-H}$ (amide)); 1638 ($\nu_{C=O}$ (amide)); 1556 ($\delta_{N-H}$ (amide)).

$^1$H-NMR spectrum (CDCl$_3$, 500 MHz, δ (ppm)): 0.88 (t, 12H, —CH$_3$); 1.25 (s, 110H, —CH$_2$—CH$_2$—, Lys ν-CH$_2$); 1.35–1.90 (br, 22H, Lys δ-CH$_2$, —CH$_2$—C—N—, —N—CO—C—CH$_2$—, Lys β-CH$_2$); 2.00–2.45 (br, 8H, —N—CO—CH$_2$—); 3.30 (br, 6H, Lys ε-CH$_2$); 3.38 (s, 3H, —O—CH$_3$); 3.43 (br, 2H, —CH$_2$—NH—); 3.66 (PEG); 4.48 (br, 3H, Lys α-CH$_2$).

$^{13}$C-NMR spectrum (CDCl$_3$, 500 MHz, δ (ppm)): 14.12; 22.68; 25.79; 26.15; 29.36; 29.42; 29.59; 29.72; 31.93; 59.03; 70.58; 71.95.

Elemental analysis for C$_{312}$H$_{619}$N$_7$O$_{121}$: Calculated value: C, 58.51; H, 9.74; N, 1.53; O, 30.22; Found value: C, 58.20; H, 10.04; N, 1.71; O, 30.05.

EXAMPLE 4

In this example, a compound (n=3) having eight chains of alkyl groups was synthesized as follows.

The stearoyl derivative 9 (50 mg, 0.043 mmol) obtained in Example 2 and DCC (8.2 mg, 0.04 mmol) were dissolved in a mixed solvent consisting of chloroform and DMF to obtain a solution, which was subsequently stirred for one hour at 25° C. Then, the resultant solution was dropped into a solution of the compound 13 (77 mg, 0.015 mmol) and dimethylaminopyridine (2 mg, 0.017 mmol) in chloroform to obtain a reaction mixture. After being stirred for 48 hours at 25° C., this reaction mixture was dropped into diethyl ether. Then, the precipitate was recovered by means of filtration. Thereafter, by making use of a silica gel column (solvent: chloroform/methanol=6/1 (vol./vol.)), an amphiphilic compound 15 of the present invention was isolated (83mg, yield: 78%).

<Results of Analysis of the Compound 15>

Thin-layer chromatography (silica gel plate, chloroform/methanol (4/1) (vol./vol.): $R_f$: 0.78 (monospot))

IR (cm$^{-1}$): 3305 ($\nu_{N-H}$ (amide)); 1638 ($\nu_{C=O}$ (amide)); 1556 ($\delta_{N-H}$ (amide)).

$^1$H-NMR spectrum (CDCl$_3$, 500 MHz, δ (ppm)): 0.88 (t, 24H, —CH$_3$); 1.25 (s, 254H, —CH$_2$—CH$_2$—, Lys ν-CH$_2$); 1.35–1.90 (br, 46H, Lys δ-CH$_2$, —CH$_2$—C—N—, —N—CO—C—CH$_2$—, Lys β-CH$_2$); 2.00–2.45 (br, 16H, —N—CO—CH$_2$—); 3.30 (br, 14H, Lys ε-CH$_2$); 3.38 (s, 3H, —O—CH$_3$); 3.66 (PEG); 4.48 (br, 7H, Lys α-CH$_2$).

EXAMPLE 5

In this example, an amphiphilic compound having an oligosaccharide as a hydrophilic moiety was synthesized as follows.

(A) L-gultamic acid (3.0 g, 20.4 mmol), p-toluenesulfonic acid (3.9 g, 20.4 mmol) and stearyl alcohol (11.0 g, 40.8 mmol) were dissolved in benzene (60 mL). The resultant solution was refluxed for 14 hours at 100° C. while removing water produced. Then, the benzene phase was washed three times using a saturated aqueous solution of sodium carbonate and three times using water. Then, the solvent was removed under a reduced pressure. The resultant residue was recrystallized from methanol at 4° C., and then, subjected to filtration and desiccation to obtain, as a white solid matter, dialkyl glutamate derivative 16 (11.7 g, yield: 88%).

From the appearance of a peak (1736 cm$^{-1}$) in IR spectrum, which is peculiar to ester linkage, the formation of the aimed compound was confirmed.

(B) Maltoheptaose (0.5 g, 0.43 mmol) and glutamic acid (0.096 g, 0.65 mmol) were dissolved in DMF. The resultant solution was stirred for 2.5 hours at 60° C. to thereby bonding the glutamic acid to the reduced terminal of the maltoheptaose. Further, by making use of DCC, the dialkyl glutamate derivative 16 was introduced via amide bond into the maltoheptaose. The resultant product was reprecipitated using acetone and washed with water to refine the product, thus obtaining a maltoheptaose derivative 17 having four chains of alkyl groups (an amphiphilic compound of the present invention) (0.4 g, yield: 60%). From the integration ratio between the terminal methyl proton of alkyl chain (0.88 ppm) and the proton of maltoheptaose moiety (2.7–6.0) as measured by means of $^1$H-NMR (DMSO-d6), it was possible to confirm the linkage of four acyl chains. Further, in the same manner as described above, a dextran derivative 18 (average molecular weight: 200,000) was obtained (yield: 50%).

EXAMPLE 6

In this example, an amphiphilic compound having oligopeptide as a hydrophilic moiety was synthesized as follows.

(A) The tetrastearoyl lysine derivative 9 (100 mg, 0.068 mmol) which was obtained in Example 2 and DCC (14 mg, 0.068 mmol) were dissolved in chloroform, and the resultant solution was then stirred for one hour at 25° C. to obtain a reaction mixture, to which N-hydroxysuccinimide (0.8 mg, 0.070 mmol) employed as an activated esterification reagent was added, and the resultant mixture was stirred for 6 hours at 25° C.

From the appearance of a peak (1730 cm$^{-1}$) in infrared absorption spectrum, which is peculiar to ester linkage, it was possible to confirm the formation of the derivative 19 wherein the carboxyl group of tetrastearoyl lysine derivative 9 was acted as an active ester.

(B) A linear oligomer (15–20-mer) of glutamic acid (100 mg) and the derivative 19 were dissolved in DMF, and the resultant solution was then stirred for 12 hours at 4° C. The resultant reaction mixture was filtered to obtain a filtrate, which was then dried under a reduced pressure. The residue was dissolved in chloroform and insoluble components were removed. Thereafter, the solution was washed three times with water. The chloroform phase was then allowed to dry, and the resultant product was recrystallized using methanol at 4° C. to thereby obtain tetraalkyl oligopeptide derivative 20 (an amphiphilic compound of the present invention) (110 mg).

EXAMPLE 7

In this example, as one example of the amphiphilic compound having protein bonded thereto, a compound having myoglobin bonded thereto was synthesized by making use of a polyoxyethylene (as a spacer) whose terminal carboxyl group was activated with succinimide.

(A) First of all, a polyoxyethylene derivative having a hydrophobic group and an activated ester group at the terminals thereof was synthesized as follows. The compound to be obtained in this case is capable of bonding with all kinds of protein having a free amino group.

Polyoxyethylene having a molecular weight of 3,000 and terminal carboxyl groups at both ends thereof (3 g, 1 mmol) and DCC (206 mg, 1 mmol) were dissolved in distilled chloroform (10 mL) and stirred for 30 minutes at 5° C. Dicyclohexyl urea which was precipitated was filtered using a glass filter (G4), after which distilled chloroform (90 mL) was added to the dicyclohexyl urea. The resultant solution was dropped into a solution of ethylene diamine anhydride (610 mg, 10.1 mmol) in chloroform and stirred for 24 hours at 0° C. The resultant reaction mixture was concentrated to dry by making use of a rotary evaporator. Unreacted ethylene diamine was removed through distillation under a reduced pressure. Then, by making use of an alumina column (solvent: chloroform/methanol/water=8/3/1), polyoxyethylene having carboxyl group at one terminal thereof and amino group at the other terminal thereof was isolated (978 mg, yield: 33%).

On the other hand, the tetrastearoyl lysine derivative 9 (100 mg, 0.068 mmol) which was obtained in Example 2 and DCC (14 mg, 0.068 mmol) were dissolved in chloroform and stirred for one hour at 25° C. to obtain a reaction mixture, to which N-hydroxysuccinimide (0.8 mg, 0.070 mmol) employed as an activated esterification reagent was added, and the resultant mixture was stirred for 6 hours at 25° C.

From the appearance of a peak (1730 cm$^{-1}$) in infrared absorption spectrum, which is peculiar to ester linkage, it was possible to confirm the formation of aimed product. This product was dropped into a solution of the aforementioned polyoxyethylene derivative (185 mg, 0.061 mmol) in chloroform and stirred for 24 hours at 25° C. The resultant reaction mixture was dropped into ether and the precipitate was recovered through the filtration thereof. The crude product was refined by making use of a silica gel column (solvent: chloroform/methanol=6/1 (vol./vol.)) to isolate an amphiphilic compound 21 having terminal carboxyl group (221 mg, yield: 81%).

EXAMPLE 8

In this example, the compound 21 obtained in Example 7 was allowed to bond with protein.

Namely, the compound 21 (100 mg, 0.022 mmol) was dissolved in 1 mL of chloroform to obtain a solution, to which DCC (4.7 mg, 0.023 mmol) and N-hydroxysuccinimide (2.6 mg, 0.023 mmol) were added. Then, the mixture was stirred for 4 hours at 5° C. The product thus formed was reprecipitated and dried in vacuum. Then, phosphate buffer solution (6.69 mL, 0.019 mmol) containing 5% by weight of myoglobin which was stabilized through the coordination of carbon monoxide was added to the aforementioned product and stirred for 24 hours under the conditions of: pH=7.4, 5° C. and light-shielding. After the filtration of resultant reaction mixture, a myoglobin derivative 22 was refined and isolated by taking it up by making use of a steric exclusion chromatography (column: Asahipak GS-520). This myoglobin derivative 22 was then lyophilized and allowed to suspend in methanol. From the disappearance of the peak (2.83 ppm) of succinimide group as well as from the appearance of peaks which are peculiar to PEG chain (3.36 ppm) and to alkyl chain (0.88, 1.24 ppm), which were detected by means of $^1$H-NMR, the linkage of the compound 21 to myoglobin was confirmed. The bonding ratio of the compound 21 to myoglobin (compound 21/myoglobin) was found 1.1 as measured by the dry weight method.

<The Structures of the Compounds 1 to 22 in the Examples>

Compound 1

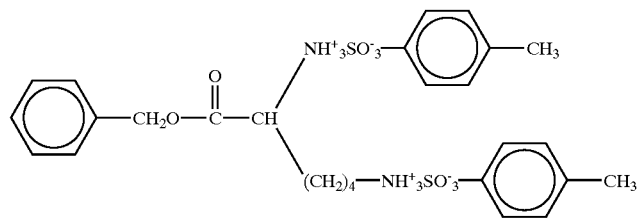

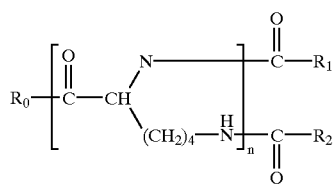

Compound 2:    $n = 1$,   $R_0 =$ —CH$_2$O,    $R_1 = R_2 = (CH_2)_{14}CH_3$

Compound 3:    $n = 1$,   $R_0 = HO$,    $R_1 = R_2 = (CH_2)_{14}CH_3$

Compound 4:    $n = 1$,   $R_0 = HO$,    $R_1 = R_2 = (CH_2)_{12}CH_3$

Compound 5:    $n = 1$,   $R_0 = HO$,    $R_1 = R_2 = (CH_2)_{16}CH_3$

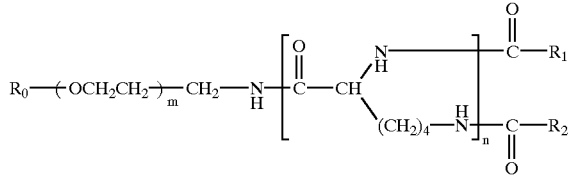

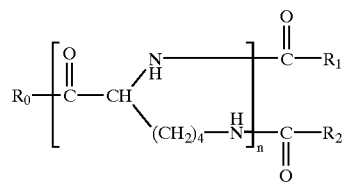

Compound 7:    $n = 2$,   $R_0 = HO$,    $R_1 = R_2 = (CH_2)_{14}CH_3$

Compound 8:    $n = 2$,   $R_0 = HO$,    $R_1 = R_2 = (CH_2)_{12}CH_3$

Compound 6:    $n = 1$,   $R_0 = CH_3$,    $R_1 = R_2 = (CH_2)_{14}CH_3$

Compound 9:    $n = 2$,   $R_0 = HO$,    $R_1 = R_2 = (CH_2)_{16}CH_3$

Compound 11

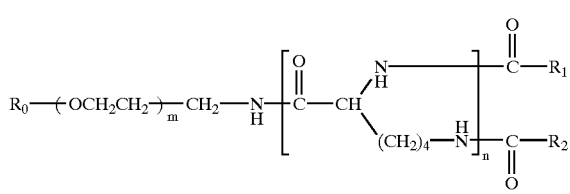

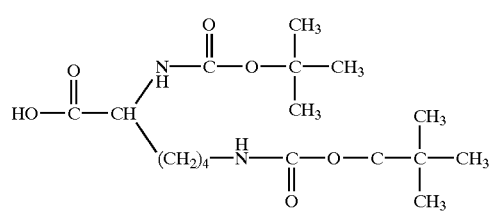

Compound 10 = 14:   $n = 2$,   $R_0 = CH_3$,   $R_1 = R_2 = (CH_2)_{14}CH_3$

Compound 12

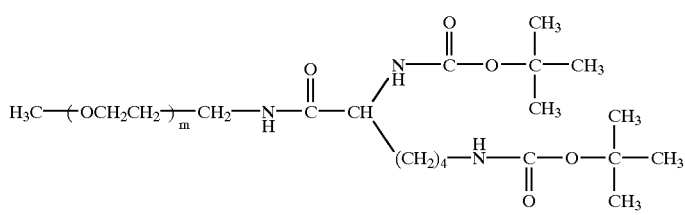

-continued
Compound 13

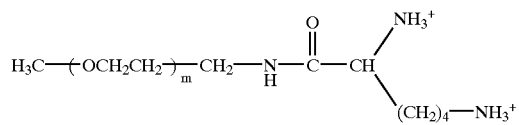

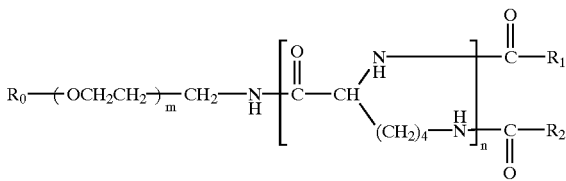

Compound 15:   n = 3,   $R_0$ = $CH_3$,   $R_1$ = $R_2$ = $(CH_2)_{16}CH_3$

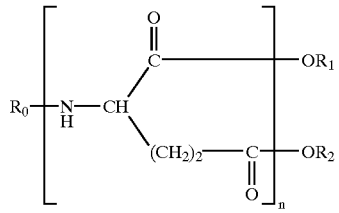

Compound 16:   n = 1,   $R_0$ = H,   $R_1$ = $R_2$ = —$(CH_2)_{16}CH_3$

Compound 17:   n = 2,   $R_0$ = maltoheptaose,   $R_1$ = $R_2$ = —$(CH_2)_{16}CH_3$ Compound 18:   n = 2,   $R_0$ = dextran,   $R_1$ = $R_2$ = —$(CH_2)_{16}CH_3$

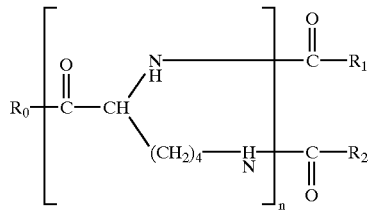

Compound 19:   n = 2,   $R_0$ = 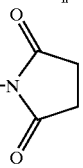,   $R_1$ = $R_2$ = $(CH_2)_{16}CH_3$

Compound 20:   n = 2,   $R_0$ = oligopeptide,   $R_1$ = $R_2$ = $(CH_2)_{16}CH_3$

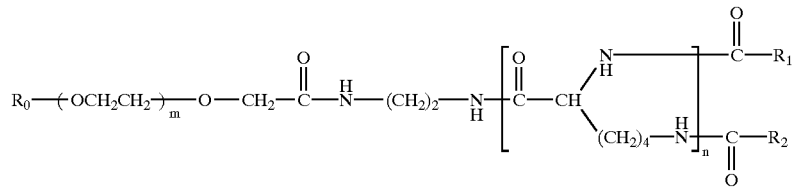

Compound 21:   n = 2,   $R_0$ = COOH,   $R_1$ = $R_2$ = $(CH_2)_{16}CH_3$

Compound 22:   n = 2,   $R_0$ = myoglobin,   $R_1$ = $R_2$ = $(CH_2)_{16}CH_3$

As explained above, it is possible according to the present invention to provide an amphiphilic compound which is capable of stably fixing a water-soluble polymer onto a surface structure by taking advantage of intermolecular interaction, thereby enabling the water-soluble polymer to be carried thereon without giving any damage to the function thereof. Further, the amphiphilic compound having a dendritic branch structure according to the present invention makes it possible to optionally balance the hydrophobic site with the hydrophilic site, and to introduce a functional polymer such as protein, through a single point bonding, into the terminal of the hydrophilic group thereof.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An amphiphilic compound having a dendritic branch structure having general formula (I):

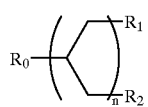
(I)

which is selected from the group consisting of an amphiphilic compound having a dendritic branch structure represented by the following formula (G), an amphiphilic compound having a dendritic branch structure represented by the following formula (H), and an amphiphilic compound having a dendritic branch structure represented by the following formula (J):

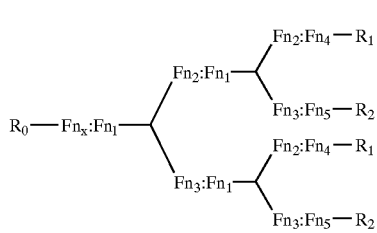
(G)

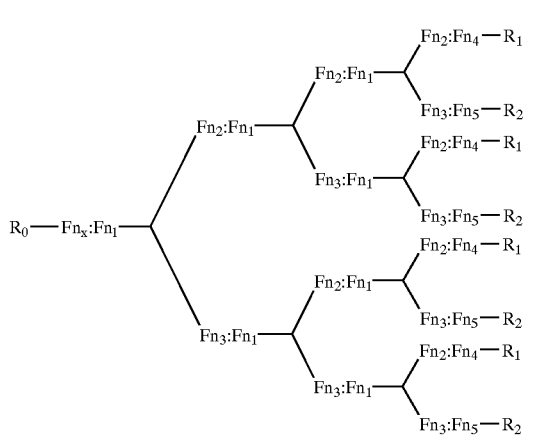
(H)

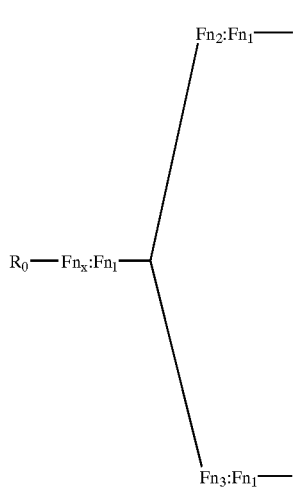
(J)

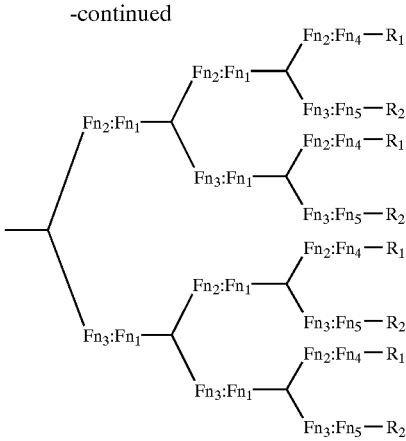

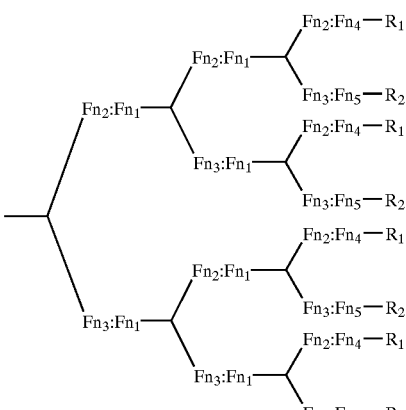

where $Fn_x$, $Fn_1$, $Fn_2$, $Fn_3$, $Fn_4$ and $Fn_5$ respectively represents a functional reactive group, each of which is bonded to a neighboring functional reactive group; $R_0$ is a poly- or oligo-oxyethylene derivative, or a poly- or oligo-saccharide derivative; $R_1$ and $R_2$ are independently a hydrophobic group; and n is an integer of 2 to 4.

2. The amphiphilic compound according to claim 1, wherein said functional reactive group is bonded through amide bond or ester bond.

3. An amphiphilic compound having a dendritic branch structure having general formula (II):

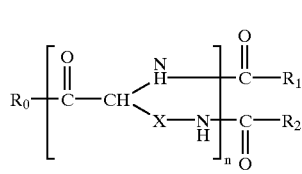
(II)

which is selected from the group consisting of an amphiphilic compound having a dendritic branch structure represented by the following formula (II-1), an amphiphilic compound having a dendritic branch structure represented by the following formula (II-2), an amphiphilic compound having a dendritic branch structure represented by the following formula (II-3), and an amphiphilic compound having a dendritic branch structure represented by the following formula (II-4):
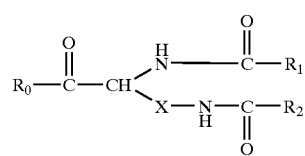
(II-1)
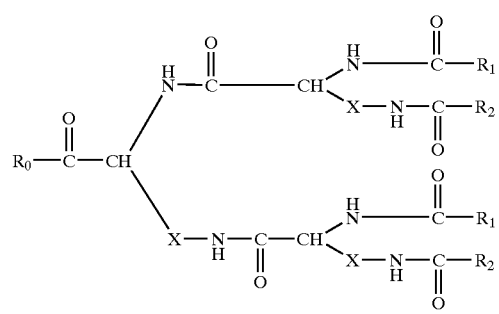
(II-2)
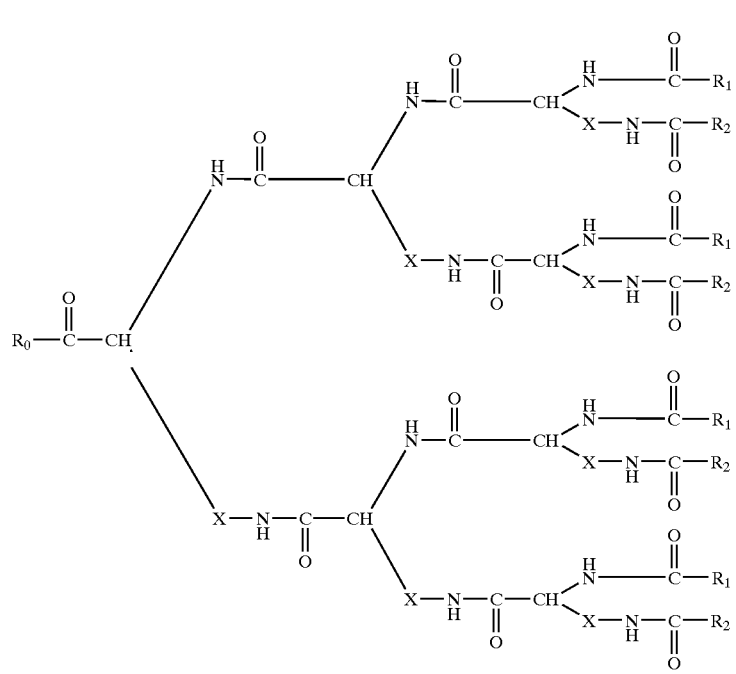
(II-3)

-continued (II-4)

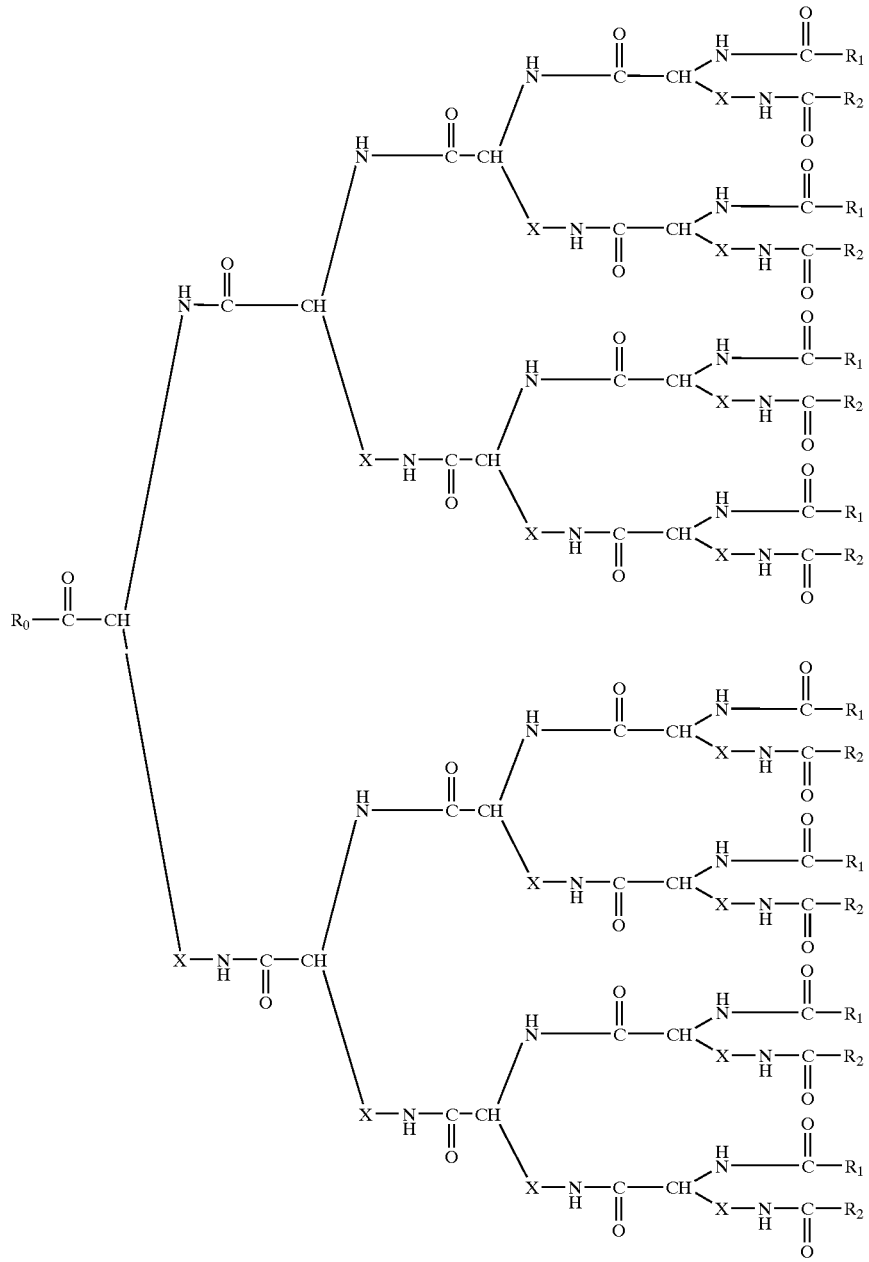

where $R_0$ is a hydrophilic group; X is —$(CH_2)_4$— or —$(CH_2)_p$—CO— (wherein p is 1 or 2); each of $R_1$ and $R_2$ is independently an alkyl group; and n is an integer of 1 to 4.

4. The amphiphilic compound according to claim 3, wherein said compound is represented by said formula (II-2), said formula (II-3) or said formula (II-4).

5. The amphiphilic compound according to claim 3, wherein said alkyl group contains 1 to 30 carbon atoms.

6. The amphiphilic compound according to claim 3, wherein said $R_0$ is poly- or oligo-oxyethylene derivative, poly- or oligo-saccharide derivative, or poly- or oligo-peptide.

7. The amphiphilic compound according to claim 4, wherein said $R_0$ is poly- or oligo-oxyethylene derivative, poly- or oligo-saccharide derivative, or poly- or oligo-peptide.

8. The amphiphilic compound according to claim 3, wherein said $R_0$ is represented by a formula:
R—$(OCH_2CH_2)_m CH_2NH$— or R—$(OCH_2CH_2)_m OCH_2C(O)NHCH_2CH_2NH$— where R is H—, $CH_3$—, $CH_3C(O)$—, $HOOCCH_2$—, $H_2NCH_2CH_2NHC(O)CH_2$—, or poly- or oligo-peptides; and m is an integer of 1 to 3000.

9. The amphiphilic compound according to claim 4, wherein said $R_0$ is represented by a formula:
R—$(OCH_2CH_2)_m CH_2NH$— or R—$(OCH_2CH_2)_m OCH_2C(O)NHCH_2CH_2NH$— where R is H—, $CH_3$—, $CH_3C(O)$—, $HOOCCH_2$—, $H_2NCH_2CH_2NHC(O)CH_2$— or poly- or oligo-peptides; and m is an integer of 1 to 3000.

10. An amphiphilic compound having a dendritic branch structure having following general formula (III):

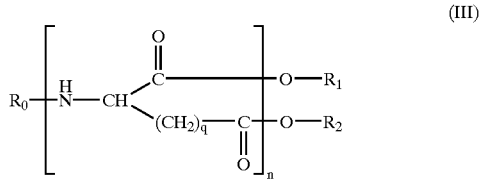

(III)

which is selected from the group consisting of an amphiphilic compound having a dendritic branch structure represented by the following formula (III-1), an amphiphilic compound having a dendritic branch structure represented by the following formula (III-2), an amphiphilic compound having a dendritic branch structure represented by the following formula (III-3), and an amphiphilic compound having a dendritic branch structure represented by the following formula (III-4):

(III-1)

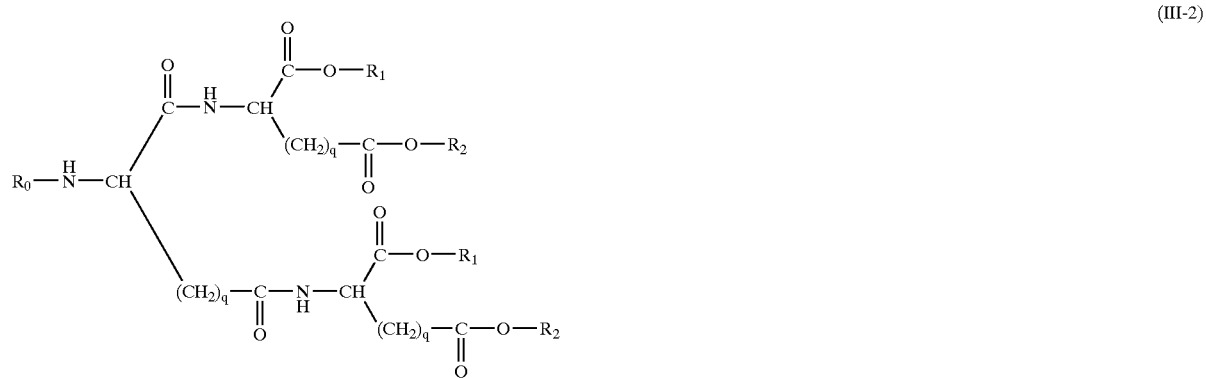

(III-2)

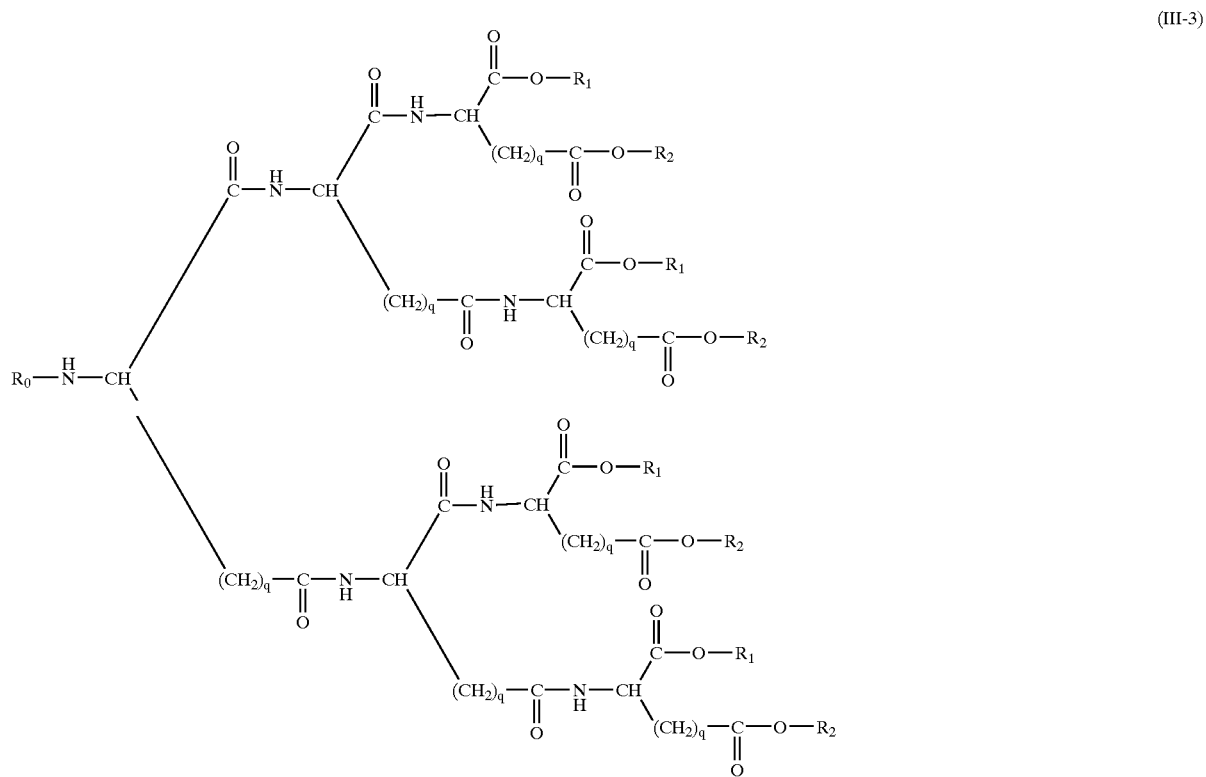

(III-3)

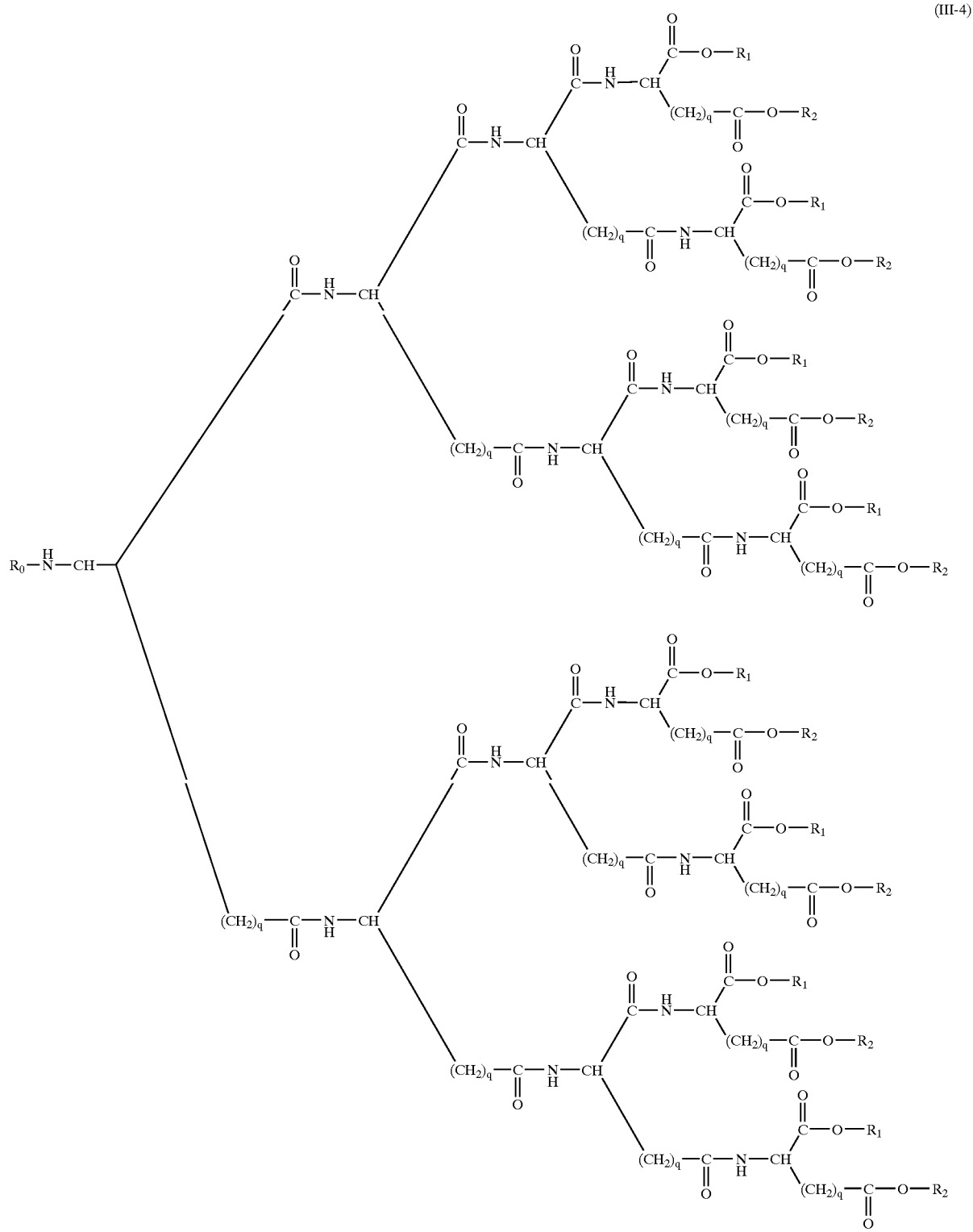

(III-4)

where $R_0$ is a hydrophilic group; each of $R_1$ and $R_2$ is independently an alkyl group; n is an integer of 1 to 4 and q is 1 or 2.

11. The amphiphilic compound according to claim 10, wherein said compound is represented by said formula (III-2), said formula (III-3) or said formula (III-4).

12. The amphiphilic compound according to claim 10, wherein said alkyl group contains 1 to 30 carbon atoms.

13. The amphiphilic compound according to claim 10, wherein said $R_0$ is poly- or oligo-oxyethylene derivative, poly- or oligo-saccharide derivative, or poly- or oligo-peptide.

14. The amphiphilic compound according to claim 11, wherein said $R_0$ is poly- or oligo-oxyethylene derivative, poly- or oligo-saccharide derivative, or poly- or oligo-peptide.

15. The amphiphilic compound according to claim 10, wherein said $R_0$ is represented by a formula:

R—$(OCH_2CH_2)_m CH_2NH$— or R—$(OCH_2CH_2)_m OCH_2 C(O)NHCH_2CH_2NH$— (wherein R is H—, $CH_3$—, $CH_3C(O)$—, $HOOCCH_2$—, $H_2NCH_2CH_2NHC(O)CH_2$— or poly- or oligo-peptides; and m is an integer of 1 to 3000.

16. The amphiphilic compound according to claim 11, wherein said $R_0$ is represented by a formula:

R—$(OCH_2CH_2)_m CH_2NH$— or R—$(OCH_2CH_2)_m OCH_2 C(O)NHCH_2CH_2NH$— wherein R is H—, $CH_3$—, $CH_3C(O)$—, $HOOCCH_2$—, $H_2NCH_2CH_2NHC(O)CH_2$— or poly- or oligo-peptides; and m is an integer of 1 to 3000.

* * * * *